US009857298B2

(12) United States Patent
Arsalan et al.

(10) Patent No.: US 9,857,298 B2
(45) Date of Patent: Jan. 2, 2018

(54) SYSTEMS AND METHODS FOR NEAR-INFRARED BASED WATER CUT MONITORING IN MULTIPHASE FLUID FLOW

(71) Applicant: Saudi Arabian Oil Company, Dhahran (SA)

(72) Inventors: Muhammad Arsalan, Dhahran (SA); Mohamed Nabil Noui-Mehidi, Dhahran (SA); Talha Jamal Ahmad, Dhahran (SA)

(73) Assignee: Saudi Arabian Oil Company (SA)

( * ) Notice: Subject to any disclaimer, the term of this patent is extended or adjusted under 35 U.S.C. 154(b) by 0 days.

(21) Appl. No.: 15/201,001

(22) Filed: Jul. 1, 2016

(65) Prior Publication Data

US 2017/0010209 A1    Jan. 12, 2017

Related U.S. Application Data

(60) Provisional application No. 62/189,060, filed on Jul. 6, 2015.

(51) Int. Cl.
*G01J 5/02*          (2006.01)
*G01N 21/359*        (2014.01)
(Continued)

(52) U.S. Cl.
CPC ............ *G01N 21/359* (2013.01); *G01F 1/661* (2013.01); *G01F 1/74* (2013.01); *G01N 21/17* (2013.01);
(Continued)

(58) Field of Classification Search
CPC .......... G01V 8/00; G01V 8/02; G01N 21/359; G01N 2201/12; G01N 2201/061; G01N 33/08
See application file for complete search history.

(56) References Cited

U.S. PATENT DOCUMENTS 4,667,515 A    5/1987   Farren et al.
5,070,725 A    12/1991  Cox
(Continued)

FOREIGN PATENT DOCUMENTS

CN    2932368 Y     8/2007
EP    0465032 A1    6/1991
(Continued)

OTHER PUBLICATIONS

Zhangshuan, H. Reservoir-parameter identification using minimum relative entrophy-based Bayesian inversion of seismic AVA and marine CSEM data, Geophysics, vol. 71, No. 6, (Nov.-Dec. 2006); pp. 077-088.
(Continued)

*Primary Examiner* — Kiho Kim
(74) *Attorney, Agent, or Firm* — Bracewell LLP; Constance Gall Rhebergen

(57) ABSTRACT

Embodiments of systems and methods for characterizing multiphase flow (MPF) of fluid and enhancing measuring and monitoring of a full range of water cut in a portion of a pipe for oil-related operations are provided. An embodiment of a system can include a flow director to direct the MPF between paired wide-band near-infrared (NIR) emitters and detectors electrically coupled to signal conditioning, processing, and characterizing modules to determine absorption and scattering of MPF and define and display MPF characteristics for measuring and monitoring in oil-related operations.

26 Claims, 6 Drawing Sheets

(51) Int. Cl.
*G01F 1/66* (2006.01)
*G01F 1/74* (2006.01)
*G01N 21/17* (2006.01)
*H04B 10/25* (2013.01)
*G01N 21/85* (2006.01)
*G01N 33/18* (2006.01)
*G01N 21/49* (2006.01)
*G01N 21/84* (2006.01)

(52) U.S. Cl.
CPC ......... *G01N 21/85* (2013.01); *H04B 10/2504* (2013.01); *G01N 21/49* (2013.01); *G01N 33/18* (2013.01); *G01N 2021/8405* (2013.01); *G01N 2201/061* (2013.01); *G01N 2201/12* (2013.01)

(56) References Cited

U.S. PATENT DOCUMENTS

| | | | |
|---|---|---|---|
| 5,146,414 | A | 9/1992 | McKown |
| 5,148,405 | A | 9/1992 | Belchamber |
| 5,207,107 | A | 5/1993 | Wolf et al. |
| 5,353,627 | A | 10/1994 | Diatschenko et al. |
| 5,415,048 | A | 5/1995 | Diatschenko et al. |
| 5,561,245 | A | 10/1996 | Georgi et al. |
| 5,619,043 | A | 4/1997 | Preikschat |
| 5,729,013 | A | 3/1998 | Bergren, III |
| 5,792,962 | A | 8/1998 | Constant |
| 6,076,049 | A | 6/2000 | Lievois |
| 6,412,352 | B1 | 7/2002 | Evans et al. |
| 6,575,043 | B1 | 6/2003 | Huang et al. |
| 6,644,119 | B1* | 11/2003 | Sinha ................. G01N 29/036 702/103 |
| 6,672,131 | B1 | 1/2004 | Aldal et al. |
| 7,075,063 | B2* | 7/2006 | Dong ...................... G01V 8/02 250/258 |
| 7,201,068 | B2 | 4/2007 | Foss |
| 7,233,001 | B2 | 6/2007 | Lievois |
| 7,274,996 | B2 | 9/2007 | Lapinski et al. |
| 7,293,471 | B2 | 11/2007 | Lund Bo |
| 7,436,514 | B2 | 10/2008 | Ludwig |
| 7,437,946 | B2 | 10/2008 | Gysling |
| 7,562,584 | B2 | 7/2009 | Conquergood |
| 7,654,155 | B2 | 2/2010 | Johansen |
| 7,775,125 | B2 | 8/2010 | Rhodes |
| 8,321,133 | B2 | 11/2012 | Hsu |
| RE44,943 | E | 6/2014 | O'Brien |
| 8,916,815 | B2 | 12/2014 | Xie |
| 9,008,762 | B2 | 4/2015 | Brockway |
| 9,689,802 | B2* | 6/2017 | Caseres ............. G01N 21/3554 |
| 2002/0029883 | A1 | 3/2002 | Vinegar et al. |
| 2007/0068242 | A1* | 3/2007 | DiFoggio .............. E21B 47/102 73/152.55 |
| 2007/0288178 | A1 | 12/2007 | Bonnefous |
| 2008/0163692 | A1 | 7/2008 | Huang et al. |
| 2009/0152475 | A1* | 6/2009 | Sasaki ...................... G01J 3/10 250/492.1 |
| 2010/0145634 | A1 | 6/2010 | Pinguet |
| 2011/0036177 | A1* | 2/2011 | Pinguet ..................... G01F 1/74 73/861.04 |
| 2012/0046870 | A1* | 2/2012 | Lievois ................... G01F 1/44 702/12 |
| 2012/0323502 | A1 | 12/2012 | Tanoura |
| 2013/0016336 | A1* | 1/2013 | Xie ........................ G01N 21/33 356/51 |
| 2014/0076547 | A1 | 3/2014 | Unalmis |
| 2014/0110105 | A1 | 4/2014 | Jones |
| 2014/0260659 | A1 | 9/2014 | Sheila-Vadde |

FOREIGN PATENT DOCUMENTS

| | | |
|---|---|---|
| EP | 2199755 A1 | 6/2010 |
| GB | 2426579 A | 11/2006 |
| WO | 9823931 A1 | 6/1998 |
| WO | 0045133 A1 | 8/2000 |
| WO | 2004063741 A2 | 7/2004 |

OTHER PUBLICATIONS

Al-Lababidi et al., "Upstream Multiphase Flow Assurance Monitoring Using Acoustic Emission", www.intechopen.com/books/acoustic-emission/multiphase-flow-assurance-monitoring-using-acoustic-emission, 2012, pp. 217-251.

Carvalho, "Application of the unitrasonic technique and high-speed filiming for the study of the structure of air-water bubbly flows", Experimental Thermal and Fluid Science, Elsevier Science Inc., New York, US, vol. 33, No. 7, Oct. 1, 2009, pp. 1065-1086.

International Search Report and Written Opinion for related PCT application PCT/US2016/038641 dated Sep. 21, 2016.

International Search Report and Written Opinion for related PCT application PCT/US2016/038660 dated Sep. 21, 2016.

International Search Report and Written Opinion for related PCT application PCT/US2016/040980 dated Oct. 24, 2016.

Gao et al., "Flow-pattern identification and nonlinear dynamics of gas-liquid two-phase flow in complex networks", Physical Review, 2009, pp. 1-14, vol. 79, The American Physical Society.

Pincus, "Approximate entropy as a measure of system complexity", Mathematics, 1991, pp. 2297-2301, vol. 88, Proceedings of the National Academy of Sciences.

Arridge, S R et al. "The use of multiple data types in time-resolved optical absorption and scattering tomography (TOAST)," Proc. SPIE. 2035 p. 218-229. (1993).

Kam Owd Water Cut Meter—by Kam Controls Inc., http://www.kam.com/kam-products/owd-oil-water-detector/ accessed Sep. 14, 2016 (2 pages).

PhaseDynamics; CCM Multiphase Metters; http://www.phasedynamics.com accessed Sep. 14, 2016 (pp. 1-5).

Roxar Watercut meter (WCM) by Emerson Process Management http://www2.emersonprocess.com/en-us/brands/roxar/flowmetering/meteringsystems/pages/roxarwatercutmeter.aspx accessed Sep. 14, 2016 (1 page).

Schlumberger "Vx Multiphase Well Testing Technology" http://www.slb.com/services/characterization/testing/multiphase/vx_technology.aspx accessed Sep. 14, 2016 (1 page).

Weatherford International "Flow Measurement" http://www.weatherford.com/en/products-services/production/flow-measurement accessed Sep. 14, 2016 (pp. 1-6).

Zelentech; Watercut monitor by Zelentech, http://www.zelentech.co/products/watercut.php accessed Sep. 14, 2016 (pp. 1-4).

Norgaard et al., "Principal Component Analysis and Near Infrared Spectroscopy", A white paper from FOSS, Nov. 16, 2012, pp. 1-7.

* cited by examiner

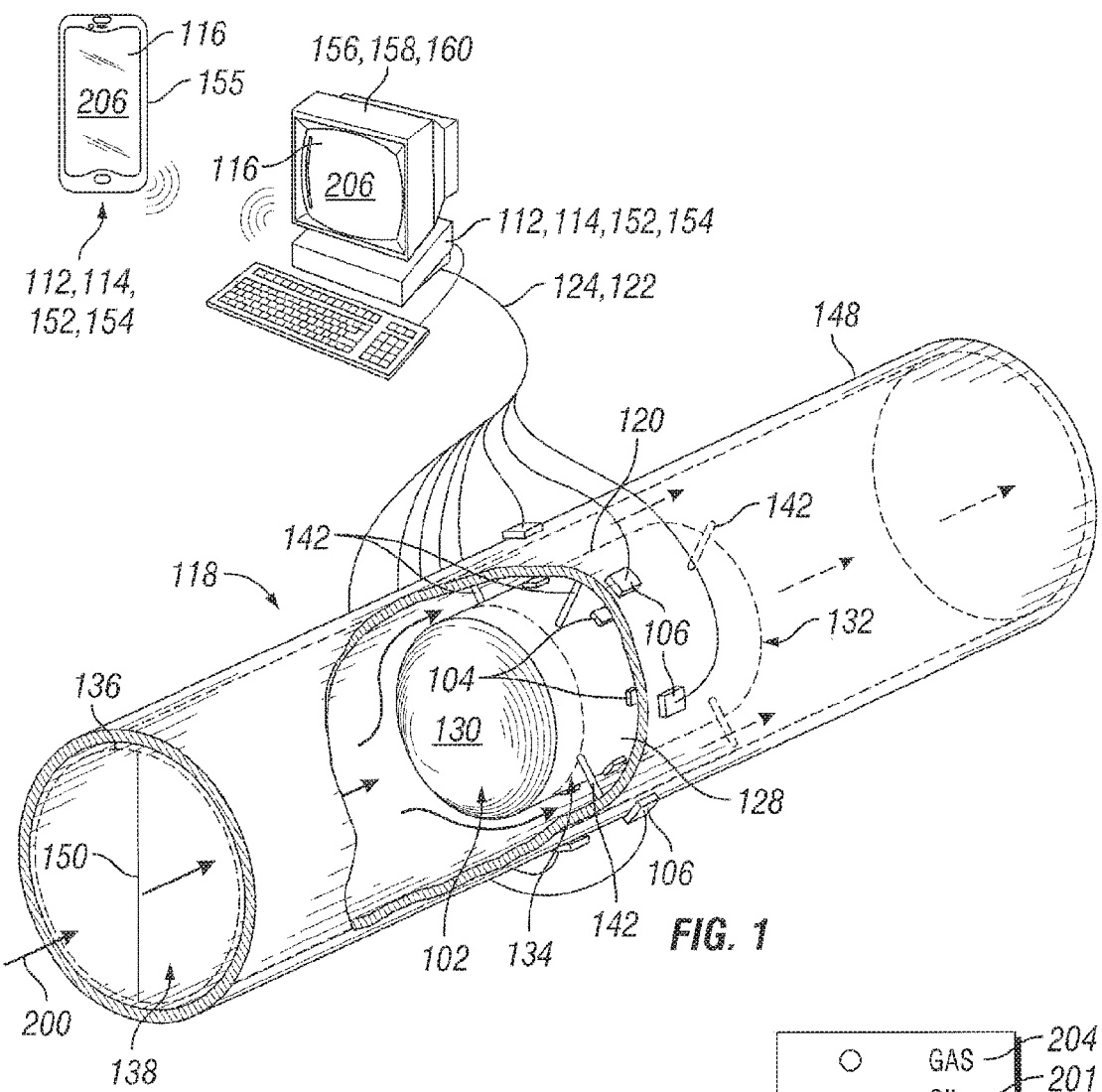
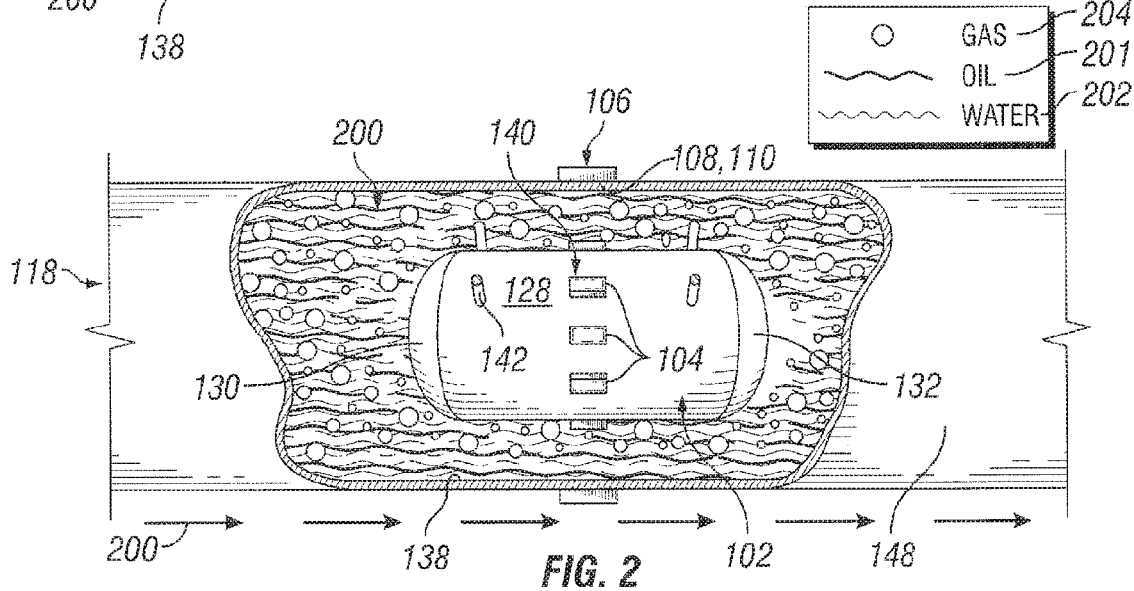

SYSTEMS AND METHODS FOR NEAR-INFRARED BASED WATER CUT MONITORING IN MULTIPHASE FLUID FLOW

CROSS-REFERENCE TO RELATED APPLICATIONS

This application claims priority to U.S. Provisional Patent Application No. 62/189,060 filed on Jul. 6, 2015.

BACKGROUND

1. Field

Embodiments of the present disclosure relate to systems and methods for measuring and monitoring characteristics of multiphase flow (MPF) of fluid in a portion of a pipe for oil-related services.

2. Description of Related Art

BACKGROUND

Multiphase flow (MPF) is simultaneous flow of materials with different states or phases (for example, gas, liquid, or solid), or materials with different chemical properties but in the same state or phase (for example, liquid-liquid systems such as oil droplets in water). MPF is a common phenomenon in the petroleum industry in the form of oil, water, gas, and other solvents. The behavior of MPF is much more complex than for single phase flow, and flow regime or flow pattern in MPF depends on a number of factors, including the relative density ratio of one fluid to the other, difference in viscosity between fluids, and velocity (for example, slip), of each respective fluid. The term "fluid flow" can include components like oil, water, gas, and solid (generally sand). An illustration of MPF can be seen in FIG. 7.

The oil and gas industry needs reliable meters to accurately measure MPF for a full range of water cut (for example, the volume of water produced compared to the total production volume). This ability to measure and characterize MPF, for example, into individual flow fractions, flow regimes, and water cut is significantly important in oil and gas operations. These characteristics are used in a variety of applications, including, for example, optimizing production, production monitoring, well testing, and water allocation. Oil-related operations can refer to any upstream or downstream production concerning hydrocarbons in any form, including, but not limited to, crude oil, natural gas, natural gas condensates, liquefied petroleum gas, heavy products, light products, and distillates.

There are several commercially available water cut and multiphase meters that use different measurement techniques, including microwaves, resonance, impedance, capacitance, conductance, gamma rays, and NIR. All of these meters, however, have shortcomings that affect, for example, the accuracy, safety, or cost of deploying the technique in the field. Capacitance and conductance based meters, for example, do no work in the phase inversion region when the flow changes its phase from oil-continuous to water-continuous or vice versa.

The meter using gamma rays is unsafe to handle due to its radioactivity. The only existing meter that uses NIR waves only measures a tiny volume of liquid that is not representative of the full MPF, and as a result, it produces large errors in low water cut measurements. Many of the techniques discussed are not suitable for downhole deployment due to frequent maintenance needs. No meter is available that can reliably measure water cut in the full range (0-100%) of oil, water, and gas fractions.

All of the proposed techniques are limited in measuring MPF of fluid over a complete range of liquid and gas flow rates. No water cut and MPF meter is commercially available that can accurately, reliably, and safely measure and characterize MPF of fluid in a full range of oil, water, and gas.

SUMMARY

It is important for oil-related operations to have technology to accurately, reliably, and safely measure and monitor characteristics of multiphase flow (MPF) in oil pipelines and in wellbores. These oil-related operations use such measuring and monitoring to, among other things, optimize production, predict water usage, and manage reservoirs. Embodiments of the system can be used, for example, at all upstream and downstream oil-related applications where reliable full range MPF and water cut meters are needed. Embodiments of systems and methods of the present disclosure also can be reliably deployed downhole in extreme reservoir contact wells as part of a permanent or retrievable system for compartmental flow monitoring to achieve tighter production control and optimization. Embodiments of systems and methods utilize safe techniques for measuring and monitoring, and embodiments of systems of the present disclosure are cost effective to implement, compact, and require little maintenance. Embodiments of the present disclosure do not suffer from the problems of the prior art water cut meters, including phase inversion problems, radioactivity of materials, failure to measure the entire range of water cut, and frequent maintenance needs.

Embodiments of systems and methods of the present disclosure are designed, for example, to safely, accurately, and reliably measure and monitor MPF, whether the MPF is scattering or non-scattering. In either case, embodiments of systems and methods can utilize, for example, a flow director positioned circumferentially within a portion of the pipe with wide-band NIR sources or optical windows mounted on it, and paired with wide-band NIR detectors mounted outside (with an optical window), inside, or integral with a portion of the pipe. Because of this close positioning, for example, MPF is directed between the paired sources and optically-aligned detectors, and embodiments of the system and method of the present disclosure use fiber optics to directly contact and facilitate the measurement of energy reflected, absorbed, and conveyed through MPF that is flowing through that portion of the pipe. This close positioning, among other reasons, allows the use of wide-band NIR signals, having wavelengths from about 350 to about 2500 nanometers with a low beam angle of about five degrees or less, to penetrate the MPF over a full range of water cut.

These detected signals can be, for example, conditioned and processed using one or more processors electrically coupled to the detectors to determine the relative absorption and scatter of the MPF. Embodiments of the present disclosure can further include computationally-efficient techniques for calculating MPF characteristics using one or more processors and software of a smartphone, general purpose computer (PC), digital signal processor (DSP), or an application-specific integrated circuit (ASIC). After the signals have been processed and analyzed according to embodiments of the present disclosure, MPF characteristics can be saved in memory and displayed on a display coupled with the smartphone, PC, DSP, or ASIC or conveyed via wires or wirelessly to a remote location, to enhance measuring and monitoring of MPF in oil-related services.

Where scattering of the NIR waves through the MPF is significant, embodiments of systems and methods can account for the scatter using, for example, optical switches, a controller, a splitter, and a single NIR source. In an embodiment, for example, an optical splitter and a controller can eliminate multiple low intensity NIR signals and promote a single higher intensity signal. This embodiment, for example, can allow the system to quantify the absorption and scattering characteristics from a single NIR source point. This embodiment can significantly enhance the accuracy of a meter designed for measuring MPF that causes significant scattering of the incoming NIR waves.

In some embodiments, the single high intensity source is about equal to a number N multiplied by the low intensity source, where N is the number of low intensity signals that the higher intensity signal will be replacing. The low intensity source(s) can be replaced by a high intensity source using relative intensity.

Embodiments of methods to directly characterize the components of MPF of fluid including, for example, oil, water, gas, and solids are disclosed, and measuring and monitoring a full range of water cut in a portion of a pipe through which the fluid flows for oil-related operations is enhanced. Methods can include, for example, directing MPF of fluid through a portion of a pipe closely adjacent to an inner surface of the portion of the pipe so that a full range of water cut flows closely adjacent the inner surface of the portion of the pipe.

Where the MPF is scattering, embodiments of methods of the present disclosure also can include controlling a wide-band NIR source positioned within the portion of the pipe to emit a high intensity wide-band NIR signal that penetrates MPF of the fluid as it flows closely adjacent the inner surface of the portion of the pipe. Directing the MPF of fluid closely towards the inner surface of the portion of the pipe will enhance detecting of the one or more high intensity wide-band NIR signals by use of a plurality of wide-band NIR detectors mounted on and spaced-apart along the outside surface of the portion of the pipe and correspondingly paired with a plurality of optical windows positioned within the portion of the pipe as MPF of fluid flows between the paired optical windows and detectors.

Embodiments of methods of the present disclosure also can include processing the one or more detected high intensity wide-band NIR signals to determine relative absorption and scatter for each of the components of MPF of fluid relative to a baseline to define one or more MPF characteristics to be displayed on one or more displays and enhance measurement and monitoring in oil-related operations within the portion of the pipe.

Embodiments of the invention include a system to characterize multiphase flow (MPF) of fluid and enhance measuring and monitoring a full range of water cut for the total flow volume in a portion of a pipe for oil-related operations, the system comprising a flow director anchored within a portion of a pipe and positioned circumferentially within and closely adjacent an inner surface of the pipe to direct MPF through the portion of the pipe for a full range of water cut towards the inner surface of the portion of the pipe; a plurality of wide-band Near-Infra Red (NIR) sources, coupled to and positioned spaced-apart along the flow director within the portion of the pipe, to generate one or more wide-band NIR signals; a plurality of wide-band NIR detectors, mounted to and positioned circumferentially along an outer surface of the portion of the pipe and being correspondingly paired through at least one optical window with the plurality of wide-band NIR sources positioned within the portion of the pipe, to detect the one or more generated wide-band NIR signals passing through a medium; a photo multiplier electrically coupled to the plurality of wide-band NIR detectors to accumulate and amplify each of the generated one or more wide-band NIR signals and the detected one or more wide-band NIR signals and one or more processors electrically coupled to the photo multiplier. Embodiments also have associated non-transitory tangible computer-readable medium and being operable by the one or more processors to execute a set of instructions comprising: processing responsive to each of an amplified generated one or more wide-band NIR signals and an amplified detected one or more wide-band NIR signals, to determine a plurality of wavelengths and corresponding frequencies associated with each of the amplified generated one or more wide-band NIR signals and the amplified detected one or more wide-band NIR signals, and analyzing the plurality of wavelengths and frequencies to determine corresponding absorption and scattering associated with each of the amplified generated one or more wide-band NIR signals and the amplified detected one or more wide-band NIR signals so that the absorption and scattering define a plurality of MPF characteristics associated with the MPF through the portion of the pipe; and one or more displays in communication with the one or more processors to display MPF characteristics to measure and monitor in oil-related operations within the portion of the pipe.

Embodiments also include where the MPF of fluid comprises non-scattering medium, and where each respective wide-band NIR detector of the plurality of wide-band NIR detectors has an optical window and an optical sensing interface positioned to enhance detecting of the generated one or more wide-band NIR signals.

Embodiments also include where the generated one or more wide-band NIR signals has a wavelength in a range of about 350 to 2000 nanometers, has a narrow beam angle of five degrees or less, and penetrates MPF of fluid without significant scattering properties, and where the flow director further is positioned closely adjacent an inner surface of the pipe to enhance close pairing of the plurality of wide-band NIR sources with the plurality of wide-band NIR detectors so that the generated one or more wide-band NIR signals penetrates the MPF.

Embodiments also include a system further comprising one or more anchors coupled to the pipe to anchor the flow director within the portion of the pipe, provide electrical access in and through the flow director and to the plurality of wide-band NIR sources, and facilitate a plurality of optic fibers being positioned.

Embodiments also include where the flow director comprises a closed cylindrical tube having a circumference just smaller than a circumference of the portion of the pipe in which the flow director is anchored, and having ends shaped to facilitate MPF traveling around the flow director so that MPF is directed between the flow director and the inner surface of the portion of the pipe.

Embodiments also include where the processing responsive to each of the amplified generated one or more wide-band NIR signals and the amplified detected one or more wide-band NIR signals comprises: performing one or more DFT operations on the amplified generated one or more wide-band NIR signals using the one or more processors to define a plurality of input DFT components for a sequence of N samples f(n), indexed by n=0 ... N−1, where the DFT operation is defined as F(k), where k=0 ... N−1:

$$F(k) = \frac{1}{\sqrt{N}} \sum_{n=0}^{N-1} f(n)e^{-j2\pi kn/N}$$

and, performing one or more DFT operations on the amplified detected one or more wide-band NIR signals using the one or more processors to define a plurality of detected DFT components for a sequence of N samples f(n), indexed by n=0 ... N−1, where the DFT is defined as F(k), where k=0 ... N−1:

$$F(k) = \frac{1}{\sqrt{N}} \sum_{n=0}^{N-1} f(n)e^{-j2\pi kn/N}.$$

Embodiments also include where the analyzing the plurality of wavelengths and frequencies to determine corresponding absorption and scattering associated with each of the amplified generated one or more wide-band NIR signals and the amplified detected one or more wide-band NIR signals further comprises comparing the plurality of input DFT components with the plurality of detected DFT components to characterize associated absorption and scattering of individual wavelengths and associated frequencies in the MPF.

Embodiments also include a system to characterize MPF of fluid and enhance measuring and monitoring a full range of water cut for the total flow volume in a portion of a pipe through which fluid flows for oil-related operations, the system comprising: a flow director anchored within a portion of a pipe and positioned circumferentially within and closely adjacent an inner surface of the pipe to direct MPF through the portion of the pipe for a full range of water cut towards the inner surface of the portion of the pipe; a wide-band Near-Infra Red (NIR) source positioned within an interior of the flow director to directly penetrate the MPF and further comprising: a wide-band NIR emitter to generate a wide-band NIR signal and optically convey the generated wide-band NIR signal to a splitter over a plurality of optic fibers; the splitter to eliminate a plurality of low intensity NIR signals from the generated wide-band NIR signal and promote optical transmission of a high intensity wide-band NIR signal to a plurality of optical switches over the plurality of optic fibers; a plurality of optical switches electrically coupled to a controller, collectively, to enhance transmission of the high intensity wide-band NIR signal to a plurality of optical windows over the plurality of optic fibers; a plurality of optical windows, coupled to and positioned spaced-apart along the flow director within the portion of the pipe, to enhance detection of the high intensity wide-band NIR signal by a plurality of wide-band NIR detectors; the plurality of wide-band NIR detectors, mounted to and positioned circumferentially along an outer surface of the portion of the pipe and being correspondingly paired with the plurality of optical windows positioned within the portion of the pipe, to detect the high intensity wide-band NIR signal passing through the MPF of fluid; a photo multiplier electrically coupled to the controller and the plurality of wide-band NIR detectors to accumulate and amplify each of the high intensity wide-band NIR signal and the detected high intensity wide-band NIR signal; one or more processors electrically coupled to the controller and the photo multiplier and having associated non-transitory tangible computer-readable medium associated and being operable by the one or more processors to execute a set of instructions comprising: processing responsive to each of an amplified high intensity wide-band NIR signal and an amplified detected high intensity wide-band NIR signal to determine a plurality of wavelengths and corresponding frequencies associated with each of the amplified high intensity wide-band NIR signal and the amplified detected high intensity wide-band NIR signal, and analyzing the plurality of wavelengths and frequencies to determine corresponding absorption and scattering associated with each of the amplified high intensity wide-band NIR signal and the amplified detected high intensity wide-band NIR signal so that the absorption and scattering define a plurality of MPF characteristics associated with the MPF through the portion of the pipe; and one or more displays in communication with the one or more processors to display the MPF characteristics to enhance measuring and monitoring in oil-related operations within the portion of the pipe.

Embodiments also include where MPF of fluid comprises scattering medium, and where each respective wide-band NIR detector of the plurality of wide-band NIR detectors has an optical sensing interface positioned to enhance detecting of the high intensity wide-band NIR signals.

Embodiments also include where the generated wide-band NIR signal has a wavelength in the range of about 350 to 2000 nanometers and has a narrow beam angle of about five degrees or less, and where the flow director further is positioned closely adjacent an inner surface of the portion of the pipe to enhance close pairing of the plurality of optical windows with the plurality of wide-band NIR detectors so that the high intensity wide-band NIR signal penetrates the MPF.

Embodiments also include a system further comprising one or more anchors coupled to the portion of the pipe to anchor the flow director within the portion of the pipe, provide electrical access in and through the flow director, and facilitate a plurality of optic fibers being positioned.

Embodiments also include where the flow director comprises a closed cylindrical tube having the interior for housing the wide-band NIR source and having a circumference just smaller than a circumference of the portion of the pipe in which the flow director is anchored, and having ends shaped to facilitate MPF traveling around the flow director so that MPF is directed between the flow director and the inner surface of the portion of the pipe.

Embodiments also include where the processing responsive to each of the amplified high intensity wide-band NIR signal and the amplified detected high intensity wide-band NIR signal comprises performing one or more DFT operations on the amplified high intensity wide-band NIR signals using the one or more processors to define a plurality of input DFT components for a sequence of N samples f(n), indexed by n=0 ... N−1, where the DFT is defined as F(k), where k=0 ... N−1:

$$F(k) = \frac{1}{\sqrt{N}} \sum_{n=0}^{N-1} f(n)e^{-j2\pi kn/N}$$

and, performing one or more DFT operations on the amplified detected high intensity wide-band NIR signal using the one or more processors to define a plurality of detected DFT components for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}.$$

Embodiments also include where the analyzing of the plurality of wavelengths and frequencies to determine corresponding absorption and scattering associated with each of the amplified high intensity wide-band NIR signal and the amplified detected high intensity wide-band NIR signal further comprises comparing the plurality of input DFT components with the plurality of detected DFT components to characterize associated absorption and scattering of individual wavelengths and associated frequencies in the MPF.

Embodiments of the invention can include a method to directly characterize MPF of fluid and enhance measuring and monitoring a full range of water cut for the total flow volume in a portion of a pipe through which the fluid flows for oil-related operations, the method comprising directing MPF through a portion of a pipe having a flow director positioned circumferentially within the portion of the pipe and closely adjacent an inner surface of the portion of the pipe so that a full range of water cut flows between the flow director and the inner surface of the portion of the pipe; inputting a plurality of wide-band Near-Infra Red (NIR) signals generated from a plurality of wide-band NIR sources mounted on and spaced-apart along the flow director that is within the portion of the pipe to penetrates the MPF as fluid flows through the portion of the pipe; detecting the generated one or more wide-band NIR signals with a plurality of wide-band NIR detectors mounted on and spaced-apart along an outside surface of the portion of the pipe through at least one optical window and being correspondingly paired with the plurality of wide-band NIR sources positioned within the portion of the pipe so that the detected one or more wide-band NIR signals can be processed; electrically communicating the generated one or more wide-band NIR signals to a photo multiplier to accumulate and amplify the generated one or more wide-band NIR signals so that the photo multiplier can electrically communicate amplified generated one or more wide-band NIR signals to the one or more processors; electrically communicating the detected one or more wide-band NIR signals to a photo multiplier to accumulate and amplify the detected one or more wide-band NIR signals so that the photo multiplier can electrically communicate amplified detected one or more wide-band NIR signals to the one or more processors; processing each of the amplified generated one or more wide-band NIR signals and the amplified detected one or more wide-band NIR signals using the one or more processors having associated non-transitory tangible computer-readable medium and being operable by the one or more processors to execute a set of instructions comprising processing responsive to each of the amplified generated one or more wide-band NIR signals and the amplified detected one or more wide-band NIR signals, to determine a plurality of wavelengths and corresponding frequencies associated with each of the amplified generated one or more wide-band NIR signals and the amplified detected one or more wide-band NIR signals, and analyzing the plurality of wavelengths and frequencies to determine corresponding absorption and scattering associated with each of the amplified generated one or more wide-band NIR signals and the amplified detected one or more wide-band NIR signals so that the absorption and scattering define a plurality of MPF characteristics associated with the MPF through the portion of the pipe; and displaying the MPF characteristics on one or more displays to enhance measurement and monitoring in oil-related operations within the portion of the pipe.

Embodiments also include where the MPF comprises non-scattering medium, and where detecting the generated one or more wide-band NIR signals with a plurality of wide-band NIR detectors is enhanced by an optical sensing interface positioned on each respective wide-band NIR detector of the plurality of wide-band NIR detectors.

Embodiments also include where the generated one or more wide-band NIR signals comprises a wavelength in the range of about 350 to 2000 nanometers and a narrow beam angle of about five degrees or less to penetrate MPF of the non-scattering medium, and where the flow director further is positioned closely adjacent an inner surface of the pipe to enhance close pairing of the plurality of wide-band NIR sources with the plurality of wide-band NIR detectors so that the generated one or more wide-band NIR signals penetrates the MPF.

Embodiments also include where the flow director comprises a closed cylindrical tube for housing the plurality of wide-band NIR sources and having a circumference just smaller than a circumference of the portion of the pipe in which the flow director is anchored, and having ends shaped to facilitate MPF traveling around the flow director so that MPF is directed between the flow director and the inner surface of the portion of the pipe.

Embodiments also include where the processing responsive to each of the amplified generated one or more wide-band NIR signals and the amplified detected one or more wide-band NIR signals comprises: performing one or more DFT operations on the amplified generated one or more wide-band NIR signals to define a plurality of input DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}$$

and, performing one or more DFT operations on the amplified detected one or more wide-band NIR signal to define a plurality of detected DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}.$$

Embodiments also include where the analyzing the plurality of wavelengths and frequencies to determine corresponding absorption and scattering associated with each of the one or more amplified generated wide-band NIR signals and the one or more amplified detected wide-band NIR signals comprises comparing the plurality of input DFT components with the plurality of detected DFT components to characterize associated absorption and scattering of individual wavelengths and associated frequencies in the MPF.

Embodiments also include a method to directly characterize MPF of fluid and enhance measuring and monitoring a full range of water cut for the total flow volume in a portion of a pipe through which fluid flows for oil-related operations, the method comprising: directing MPF through a portion of a pipe having a flow director positioned circumferentially within the portion of the pipe and closely adjacent an inner surface of the portion of the pipe so that a full range of water cut flows between the flow director and the inner surface of the portion of the pipe controlling a wide-band Near-Infra Red (NIR) source positioned within an interior of the flow director to account for scattering properties of the MPF further comprising inputting a wide-band NIR signal generated from a wide-band NIR emitter and optically conveying the generated wide-band NIR signal to a splitter over a plurality of optic fibers; splitting the generated wide-band NIR signal via a splitter to eliminate a plurality of low intensity NIR signals from the generated wide-band NIR signal and promote optical transmission of a high intensity wide-band NIR signal to a plurality of optical switches over the plurality of optic fibers; and coordinating selective transmission of the high intensity wide-band NIR signal via a plurality of optical switches and a controller to convey the high intensity wide-band NIR signal to a plurality of optical windows; enhancing transmission and reception of the high intensity wide-band NIR signal by the plurality of optical windows mounted on and spaced-apart along the flow director within the portion of the pipe so that the high intensity wide-band NIR signal penetrates the MPF as MPF flows through the portion of the pipe; detecting the high intensity wide-band NIR signal by a plurality of wide-band NIR detectors mounted on and spaced-apart along the outside surface of the portion of the pipe and being correspondingly paired with the plurality of optical windows positioned within the portion of the pipe so that a detected high intensity wide-band NIR signal can be processed; and electrically communicating the high intensity wide-band NIR signal to a photo multiplier to accumulate and amplify the high intensity wide-band NIR signal so that the photo multiplier can electrically communicate the amplified high intensity wide-band NIR signal to the one or more processors; electrically communicating the detected high intensity wide-band NIR signal to a photo multiplier to accumulate and amplify the detected high intensity wide-band NIR signal so that the photo multiplier can electrically communicate an amplified detected wide-band NIR signal to the one or more processors; processing each of the amplified high intensity wide-band NIR signal and the amplified detected wide-band NIR signal by the one or more processors having associated non-transitory tangible computer-readable medium and being operable by the one or more processors to execute a set of instructions further comprising: processing responsive to each of the amplified high intensity wide-band NIR signal and the amplified detected wide-band NIR signal, to determine a plurality of wavelengths and corresponding frequencies associated with each of amplified high intensity wide-band NIR signal and the amplified detected wide-band NIR signal, and analyzing the plurality of wavelengths and frequencies to determine corresponding absorption and scattering associated with each of the amplified high intensity wide-band NIR signal and the amplified detected wide-band NIR signal so that the absorption and scattering define a plurality of MPF characteristics associated with the MPF through the portion of the pipe; and displaying the MPF characteristics on one or more displays to enhance measurement and monitoring in oil-related operations within the portion of the pipe.

Embodiments also include where inputting a plurality of wide-band NIR signals generated from a plurality of wide-band NIR sources comprises the generated wide-band NIR signal having a wavelength in the range of about 350 to 2000 nanometers and a narrow beam angle of about five degrees or less, and where the flow director further is positioned closely adjacent an inner surface of the portion of the pipe to enhance close pairing of the plurality of optical windows with the plurality of wide-band NIR detectors so that the high intensity wide-band NIR signal penetrates the MPF.

Embodiments also include where the flow director comprises a closed cylindrical tube having the interior for housing the wide-band NIR source and having a circumference just smaller than a circumference of the portion of the pipe in which the flow director is anchored, and having ends shaped to facilitate MPF traveling around the flow director so that MPF is directed between the flow director and the inner surface of the portion of the pipe.

Embodiments also include where the processing responsive to each of the one or more amplified high intensity wide-band NIR signals and the one or more amplified high intensity wide-band NIR signals comprises: performing one or more DFT operations on the amplified high intensity wide-band NIR signal to define a plurality of input DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N}$$

and, performing one or more DFT operations on the amplified detected high intensity wide-band NIR signal to define a plurality of detected DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N}.$$

Embodiments also include where the analyzing the plurality of wavelengths and frequencies to determine corresponding absorption and scattering associated with each of the amplified high intensity wide-band NIR signal and the amplified detected wide-band NIR signal comprises comparing the plurality of input DFT components with the plurality of detected DFT components to characterize associated absorption and scattering of individual wavelengths and associated frequencies in the MPF.

Embodiments also include a method to directly characterize MPF of fluid and enhance measuring and monitoring a full range of water cut in a portion of a pipe through which the fluid flows for oil-related operations, the method comprising: directing MPF of fluid through a portion of a pipe closely adjacent an inner surface of the portion of the pipe so that a full range of water cut flows closely adjacent the inner surface of the portion of the pipe, the MPF of fluid further comprising a plurality of components of oil, water, gas, and solid; controlling a wide-band NIR source positioned within the portion of the pipe to emit a high intensity wide-band NIR signal that penetrates MPF of the fluid as it flows closely adjacent the inner surface of the portion of the pipe; detecting one or more high intensity wide-band NIR signals by use of a plurality of wide-band NIR detectors mounted on and spaced-apart along the outside surface of the portion of the pipe and correspondingly paired with a plurality of optical windows positioned within the portion of the pipe, the plurality of wide-band NIR detectors and the plurality of optical windows collectively operate to enhance detection of the high intensity wide-band NIR signal as MPF of fluid passes therebetween; and processing the one or more detected high intensity wide-band NIR signals to determine relative absorption and scatter for each component of the plurality of components in the MPF of fluid relative to a baseline to define one or more MPF characteristics to be displayed on one or more displays and enhance measurement and monitoring in oil-related operations within the portion of the pipe.

BRIEF DESCRIPTION OF DRAWINGS

The foregoing aspects, features, and advantages of embodiments of the present disclosure will further be appreciated when considered with reference to the following description of embodiments and accompanying drawings. In describing embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

FIG. 1 is a perspective view of an embodiment of the present disclosure with a portion broken away for clarity.

FIG. 2 is a side view of an embodiment of the present disclosure with a portion broken away for clarity.

DETAILED DESCRIPTION

The foregoing aspects, features, and advantages of the present disclosure will be further appreciated when considered with reference to the following description of embodiments and accompanying drawings. In describing the embodiments of the disclosure illustrated in the appended drawings, specific terminology will be used for the sake of clarity. However, the disclosure is not intended to be limited to the specific terms used, and it is to be understood that each specific term includes equivalents that operate in a similar manner to accomplish a similar purpose.

Optical Properties of Multiphase Flow (MPF)

Figure 3:
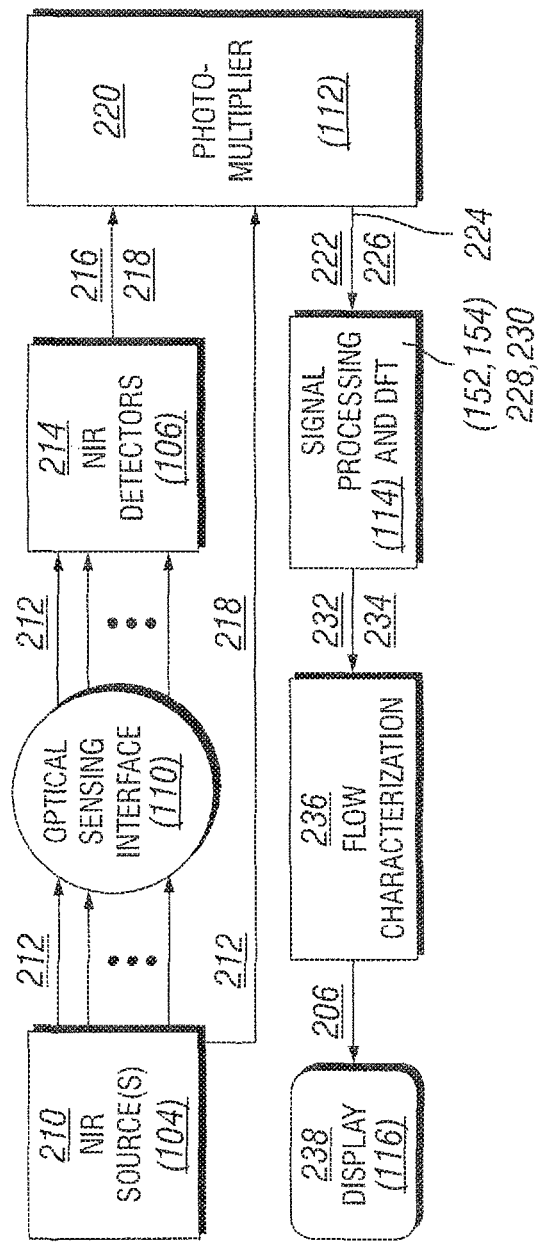
FIG. 3 is a block diagram of an embodiment of the present disclosure.
Figure 4:
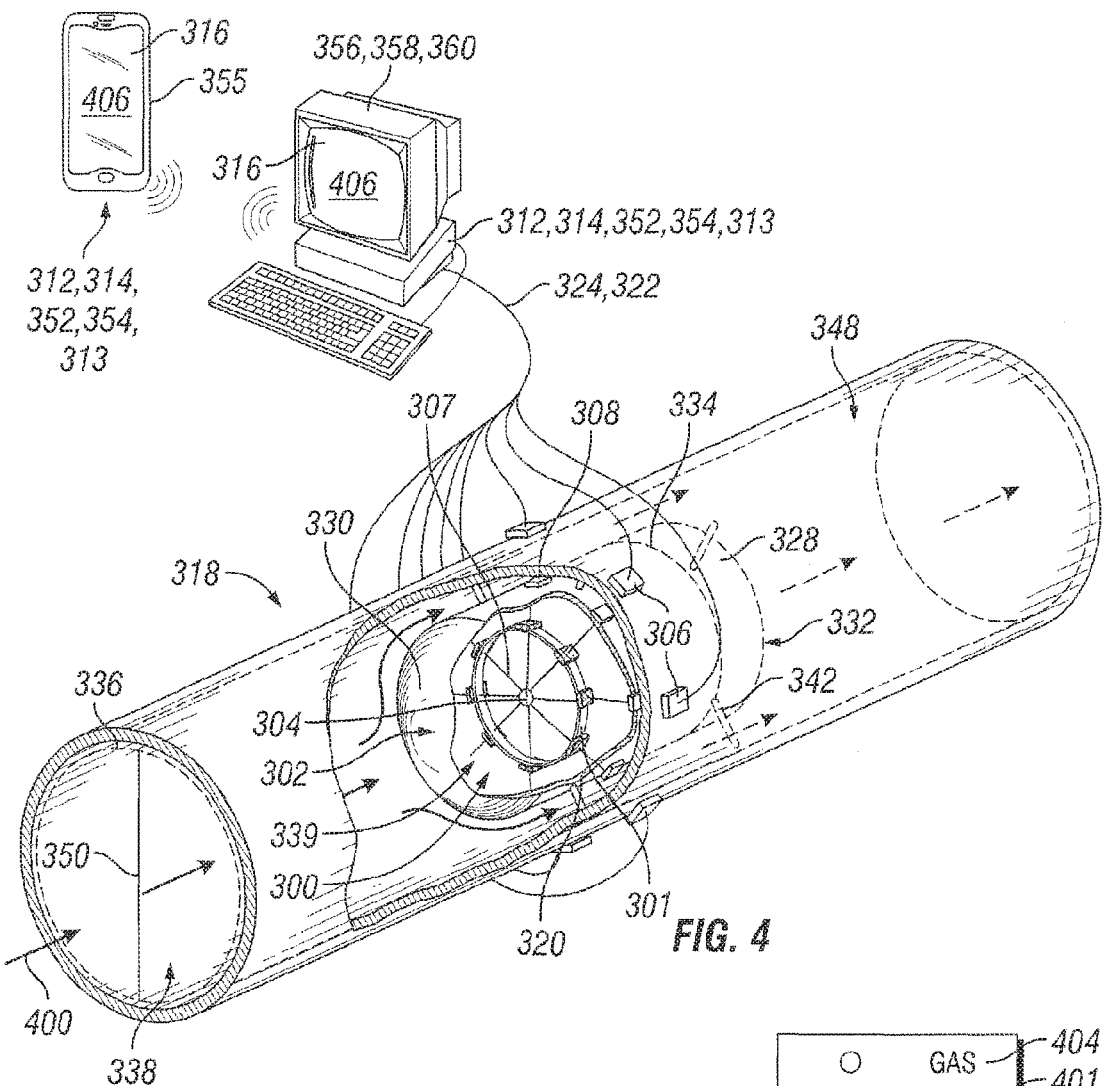
FIG. 4 is a perspective view of an embodiment of the present disclosure with portions broken away for clarity.
Figure 5:
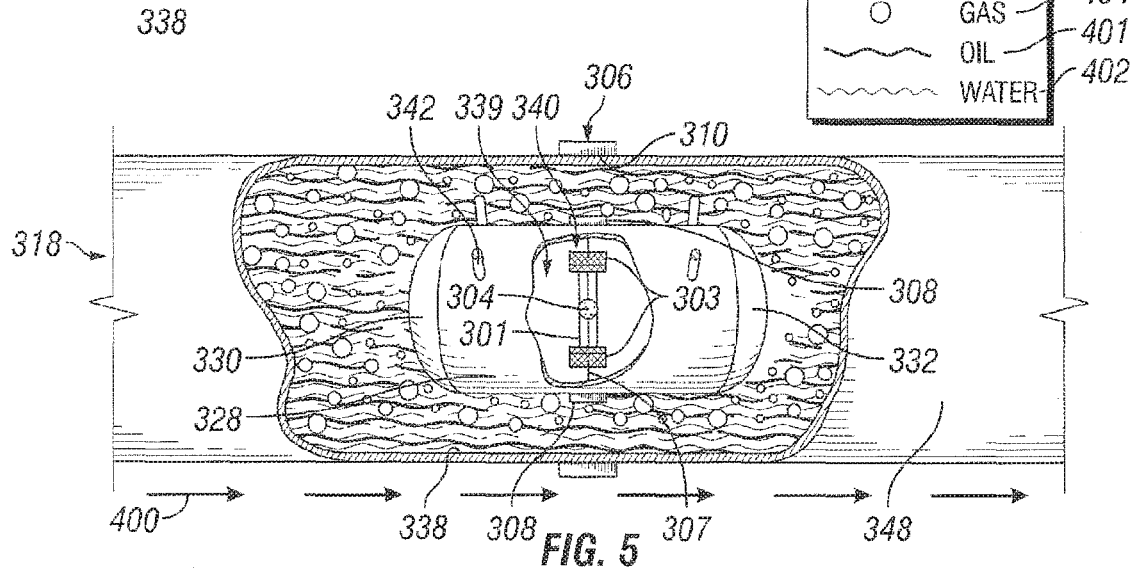
FIG. 5 is a side view of an embodiment of the present disclosure with a portion broken away for clarity.
Figure 6:
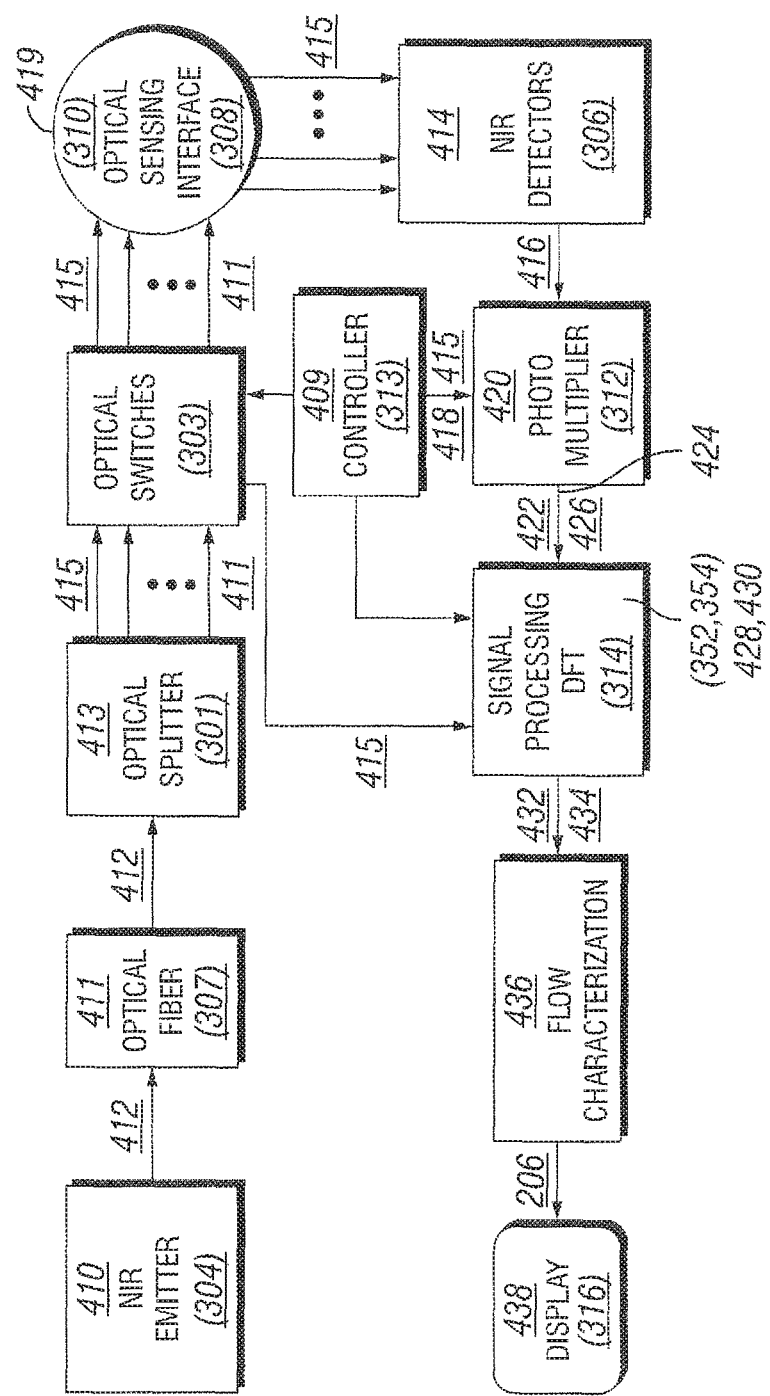
FIG. 6 is a block diagram of an embodiment of the present disclosure.
Figure 7:
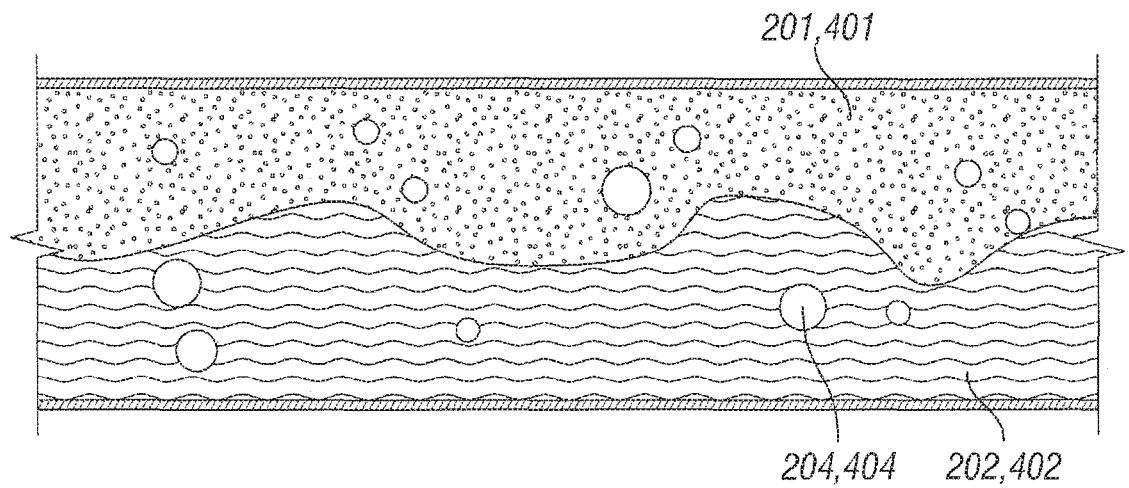
FIG. 7 shows multiphase flow (MPF) of fluid.
Figure 8:
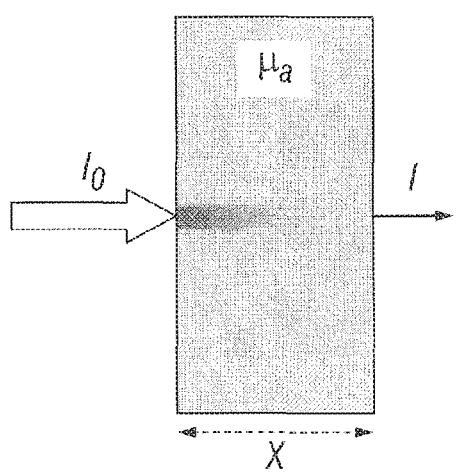
FIG. 8 shows attenuation of light through a non-scattering medium.

It is important first to understand the optical properties of MPF recognized by Applicants before further describing details of embodiments of systems and methods of the present disclosure. The optical properties of MPF are primarily described in terms of absorption and scatter. The scatter includes diffraction and reflection. If the medium is non-scattering and illuminated with a collimated beam of light of intensity ($I_0$) and wavelength ($\lambda$), then the intensity of the emerging light (I) can be calculated according to Equation 1, and as shown in FIG. 8.

$$I = I_0 e^{-\mu_a(\lambda)x} \qquad \text{Eq. (1)}$$

Equation (1) shows the absorption coefficient of the medium ($\mu_a(\lambda)$) and the width of the sample (x). The absorption coefficient represents the probability per unit length of a photon being absorbed. The absorption coefficient ($\mu_a(\lambda)$) of a medium can be due to a number of absorbing substances (oil, water, gas, and any other solids), mixed together. The individual extinction coefficients of each substance represent their absorption at a particular concentration. The absorption coefficient of a mixture of substances can be expressed as the sum of the products of the concentration of each substance ($c_n$) with its extinction coefficient ($\epsilon_n$), as shown in Equation (2).

$$\mu_a(\lambda) = \Sigma_n \epsilon_n(\lambda) c_n \qquad \text{Eq. (2)}$$

Figure 9:
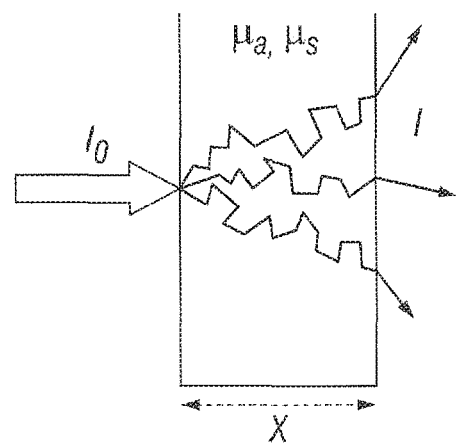
FIG. 9 shows attenuation of light through a scattering medium.
Figure 10:
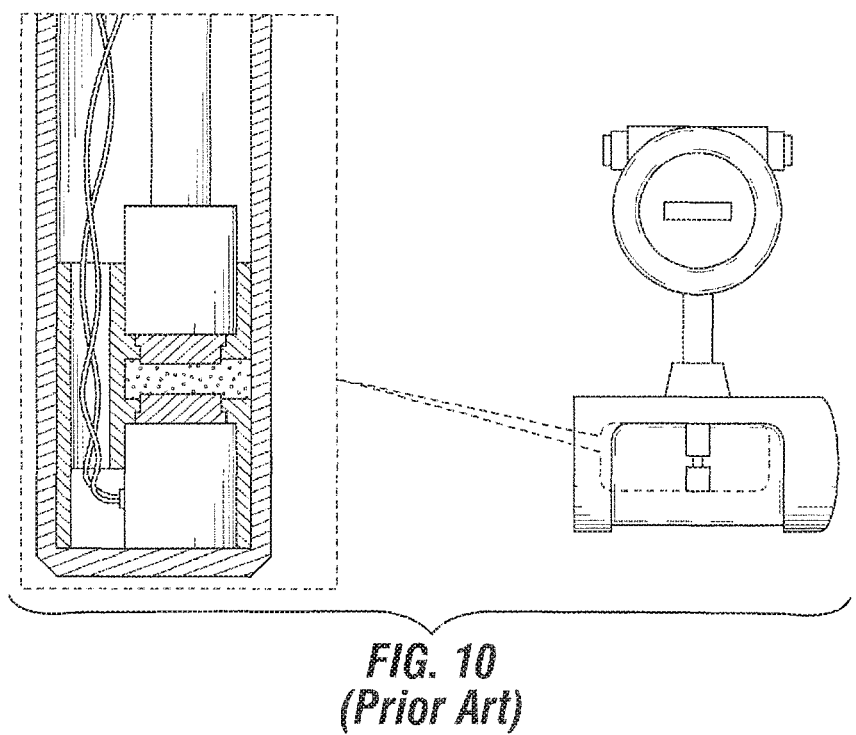
FIG. 10 is a partial cross-sectional view of a commercially available NIR water cut meter.

The scattering properties of a medium are described by its scattering coefficient ($\mu_s$). The scattering coefficient is the product of the number density of scattering particles and the scattering cross-section of the particles. Therefore, the scattering coefficient ($\mu_s$) represents the probability per unit length of a photon being scattered. Compared to the non-scattering case discussed previously, if a medium is scattering the paths taken by the photons traversing it are no longer direct. Hence, in scattering medium, all the emerging photons can no longer be detected unless the detector can collect over all angles, and at all points, on the surface of the medium. Furthermore, the photons will have travelled varying distances through the scattering media, as shown in FIG. 9.

If the medium is absorbing (which is invariably true) the increased distance travelled by photons (for example, pathlength), will attenuate them in accordance with Equation (1) where (x) is equal to or greater than the product of the differential pathlength factor ("DPF") and (x). The additional distance travelled by each photon (given by the DPF), will depend on how many scattering events it has encountered. DPF is a function of the scattering coefficient ($\mu_s$), the anisotropy of the scatter (g), the absorption of the medium and also of the geometry of the medium. Attenuation through simple scattering materials can hence be described by the modified Beer Lambert law shown as follows in Equation (3).

$$I = I_0 e^{-\mu_a(\lambda)DPFx+G} \qquad \text{Eq. (3)}$$

In Equation (3), (G) represents losses due to the geometry. Since (G) is very difficult to quantify, most simple spectroscopy looks at changes in absorption given by Equation (4).

$$\Delta A_{(2-1)} = \text{Log}\left(\frac{I_1}{I_2}\right) = DPFx(\Delta\mu_{a(2-1)}) \qquad \text{Eq. (4)}$$

In Equation (4), ($\Delta A_{(2-1)}$) is the change in attenuation measured between state 2 and state 1 corresponding to an absorption change of ($\Delta\mu_{a(2-1)}$), assuming that all other terms are constant for the two measurements. DPF can be approximately calculated based on absorption ($\mu_a$) and scatter ($\mu_s$) and the geometry of the object (for example, Arridge), or determined, for example, via measurement of the mean-time taken for light to traverse a scattering medium (<t>) using Equation (5).

$$DPF = \frac{c\langle t \rangle}{xn} \qquad \text{Eq. (5)}$$

In Equation (5), (n) is the refractive index of the material and (c) is the speed of light.

The medium described can almost invariably have absorption. Whether or not the media is scattering will determine whether the system and method of the present disclosure should account for scattering in determining MPF characteristics for measuring and monitoring.

Where MPF 200 has insignificant scatter that can be ignored, embodiments of a system of the present disclosure to characterize MPF 200 and to enhance measuring and monitoring for oil-related operations can include, for example, a flow director 102, one or more wide-band NIR sources or emitters 104, one or more wide-band NIR detectors 106 having optical windows 108 and an optical sensing interface 110, a photo multiplier 112, one or more processors 114, and one or more displays 116.

The flow director 102 can be made of metal or silicon, for example, and is anchored within the inside of a portion of a pipe 118 through which MPF 200 flows. The walls 120 of the flow director 102 can be hollow and can also contain optic fibers 122 and electrical wires 124 within it. The flow director 102 can, for example, conduct an electrical NIR signal 212 across its surface so that the electrical NIR signal 212 can be conveyed through an optic fiber 122 or electrical wire 124 from within it and can be in direct contact with the MPF 200 as the MPF 200 contacts the outer surface 128 of the flow director 102 within the portion of the pipe 118. The flow director 102 can be shaped like a closed cylindrical tube having two ends 130, 132. The largest circumference 134 of the flow director 102 can be smaller than the circumference 136 of the inner surface 138 of the portion of the pipe 118 carrying MPF 200. The flow director 102 can have a hollow or solid interior, for example, and it also can contain various other features of embodiments of the present disclosure, including for example, other electronics.

Each end 130, 132 of the flow director 102 can be rounded or pointed to facilitate MPF 200 traveling past the first end 130 in the direction of flow of the MPF 200. The plurality of NIR sources 104, detectors 106, and other electronics can be positioned approximately in the middle 140 of the flow director 102 to enable the MPF 200 to pass by the NIR sources 104, detectors 106, and other electronics as MPF 200 passes between flow director 102 and the inner surface 138 of the portion of the pipe 118 at the largest point of circumference 134, and at the shortest distance to the inner surface 138 of the portion of the pipe 118, of the flow director 102.

The flow director 102 is anchored within the portion of the pipe 118 using anchors 142 for fasteners. These anchors 142 or fasteners, for example, also can be hollow or manufactured to facilitate optic fibers 122 and electrical wires 124 within them to be in electric communication with the flow director 102. The flow director 102 and the anchors 142 can be manufactured as a single structure, or as separate structures that are later fastened together using commercially acceptable means, including, for example, by welding, soldering, and gluing.

Figure 11:
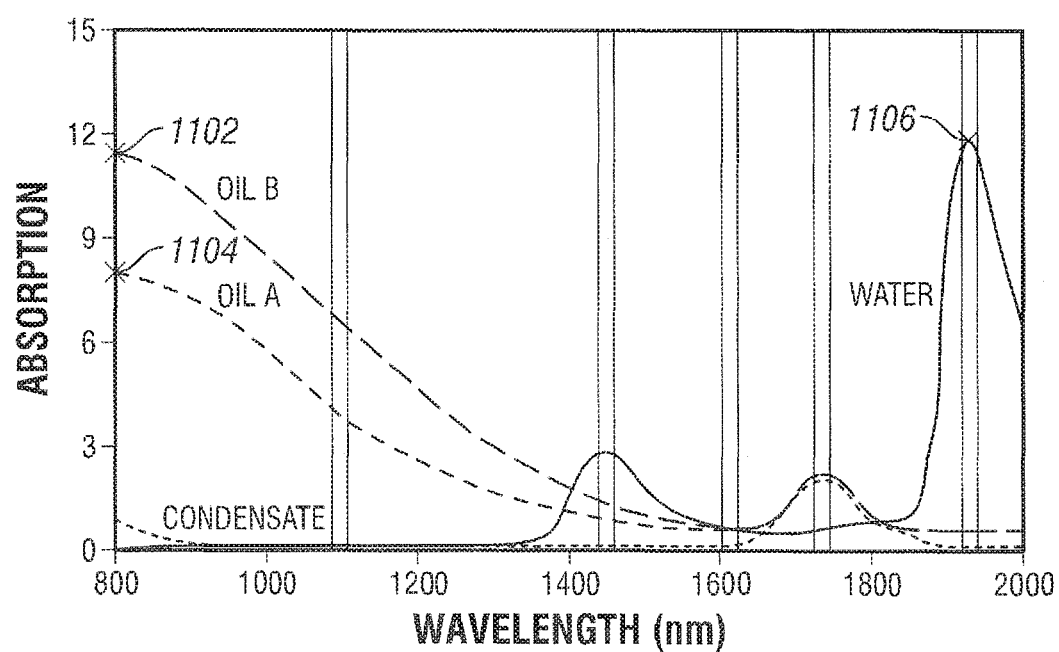
FIG. 11 is a table showing relative absorption of NIR wavelengths by different media from a commercially available NIR water cut meter.

Embodiments of a system also can include one or more wide-band NIR sources 104 or emitters for generating one or more wide-band NIR signals 212. These sources 104 can be mounted, for example, on the flow director 102 within the portion of the pipe 118 conducting MPF 200. Each source 104 can be spaced-apart from another source 104 along the flow director 102 all around the circumference 134 of the flow director 102. These sources 104 generate one or more wide-band NIR signals 212 having a wavelength, for example, between approximately 350 and 2500 nanometers, and a narrow beam angle (less than approximately 5 degrees). Wide-band NIR signals 212 having these wavelengths are useful for measuring the absorption of relative concentrations of the energy among different kinds of oils and water. As described in the graph from Unalmis, and as shown in FIG. 11, absorption of NIR waves is higher and different for each respective kind of oil 1102, 1104 at smaller wavelengths, whereas absorption of NIR waves is higher for water 1106 at larger wavelengths.

Embodiments of a system of the present disclosure also further can include one or more wide-band NIR detectors 106 mounted on the outside surface 148 of (with an optical window), or integral with, a portion of the pipe 118 conveying MPF 200. Each detector 106 can be spaced-apart from another detector 106 and correspondingly paired with the one or more wide-band NIR sources 104 mounted on the flow director 102. Each detector 106 can have, for example, an optical window 108 and an optical sensing interface 110, each for enhancing receiving of one or more wide-band NIR signals 212. The detectors 106 can electronically convey the one or more detected wide-band NIR signals 216 to electronics for signal processing, including, for example, a photo multiplier 112 and one or more processors 114.

The flow director 102 can be anchored from inside the portion of the pipe 118, and can further be positioned, for example, circumferentially within and closely adjacent the inner surface 138 of the pipe. When the MPF 200 travels through the portion of the pipe 118 containing the flow director 102, the flow director 102 directs the MPF 200 towards the inner surface 138 of the portion of the pipe 118 so that the MPF 200 passes between the paired wide-band NIR sources 104 and detectors 106. This positioning of the flow director 102 within the portion of the pipe 118 enables embodiments of the system and method of the present disclosure to accurately measure MPF 200 through a portion of a pipe 118 at a full range of water cut (from 0-100%) for oil 201, water 202, and gas 204. Even in a portion of a pipe 118 having a large diameter 150, the closely adjacent positioning of the flow director 102 to the inner surface 138 of the portion of the pipe 118, and therefore the close positioning of each pair of wide-band NIR sources 104 and detectors 106, will facilitate the wide-band NIR sources 104 to penetrate the MPF 200 using low power and low intensity signals by minimizing the distance between the paired wide-band NIR sources 104 and detectors 106.

For example, NIR signals 212 can be low power and low intensity signals. The flow director 102 will force all the MPF 200 from the annulus which will result in increasing the speed of the MPF. The ratio (f/v) of the frequency (f) of the NIR signal 212 to the fluid velocity of the MPF (v) will still be very high to effectuate desired measurements. These measurements can include, for example, the amount of energy that is absorbed, reflected, and scattered by the MPF 200. Those MPF characteristics 206 (for example, the amount of energy that is absorbed, reflected, and scattered), then can be electrically communicated from the detectors 106 to a photo multiplier 112 and one or more processors 114 for analysis and output.

In some embodiments, the single high intensity source is about equal to a number N multiplied by the low intensity source, where N is the number of low intensity signals that the higher intensity signal will be replacing. The low intensity source(s) can be replaced using relative intensity.

In some embodiments, the wavelength of the near-infrared source is about 350 to about 2500 nanometers (nm). In some embodiments, the corresponding frequency of the near-infrared source is about 856-120 terahertz (THz). In some embodiments, the velocity of fluid is from about 0.1 meter/s (m/s) to about 100 m/s.

Embodiments of a system of the present disclosure also further can include, for example, a photo multiplier 112 in electronic communication with the one or more wide-band NIR detectors 106. A photo multiplier 112 or similar signal conditioning element can be used to accumulate and amplify the one or more detected wide-band NIR signals 216 received by the detectors 106. Once the signal 216 has been amplified to define an amplified detected one or more wide-band NIR signals 226, it can be electronically communicated to one or more processors 114.

Embodiments of a system of the present disclosure also can include one or more processors 114 having associated non-transitory tangible computer-readable medium 152 and being operable by the one or more processors 114 to execute a set of instructions 154. These one or more processors 114 can be found, for example, in a smartphone 155, PC 156, DSP 158, or an ASIC 160. The set of instructions 154 (for example, software) can include, for example, processing responsive to each of the amplified one or more wide-band NIR signals 222 and the amplified detected one or more wide-band NIR signals 226, to determine a plurality of wavelengths and corresponding frequencies associated with each of the amplified one or more wide-band NIR signals 222 and the amplified detected one or more wide-band NIR signals 226. Analyzing the plurality of wavelengths and frequencies follows to determine corresponding absorption and scattering associated with each of the amplified one or more wide-band NIR signals 222 and the amplified detected one or more wide-band NIR signals 226 so that the absorption and scattering define a plurality of MPF characteristics 206 associated with the MPF 200 through the portion of the pipe 118.

The processing further comprises converting the time domain signal into the frequency domain by performing the operation of Discrete Fourier Transform (DFT) using the one or more processors 114. Given a sequence of N samples f(n), indexed by n=0 . . . N−1, the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

The one or more processors 114 will compare the DFT of the input signal with the detected DFT components to analyze the associated absorption and scattering of individual wavelength and frequency components in the MPF 200 to define MPF characteristics 206.

Where MPF 200 has insignificant scatter that can be ignored, embodiments of a method of the present disclosure can include, for example, directing MPF 200 through a portion of a pipe 118 having a flow director 102 positioned circumferentially within the portion of the pipe 118 and closely adjacent to an inner surface 138 of the portion of the pipe 118 so that a full range of water cut flows between the flow director 102 and the inner surface 138 of the portion of the pipe 118.

Embodiments of a method of the present disclosure also can include, for example, inputting 210 a plurality of wide-band NIR signals 212 generated from a plurality of wide-band NIR sources 104 mounted on and spaced-apart along the flow director 102 within the portion of the pipe 118 into the portion of the pipe 118 so that the plurality of wide-band NIR signals 212 penetrates the MPF 200 as it flows through the portion of the pipe 118, and detecting 214 the one or more generated wide-band NIR signals 212 with a plurality of wide-band NIR detectors 106 each having an optical sensing interface 110 and mounted on and spaced-apart along the outside surface 148 of the portion of the pipe 118 and being correspondingly paired with the plurality of wide-band NIR sources 104 positioned within the portion of the pipe 118 so that the detected one or more wide-band NIR signals 216 can be processed.

Embodiments of a method of the present disclosure also can include, for example, electrically communicating 218 the one or more generated wide-band NIR signals 212 to a photo multiplier 112 to accumulate and amplify 220 the one or more generated wide-band NIR signals 212 to define one or more amplified generated signals 222 so that the photo multiplier 112 can electrically communicate 224 the one or more amplified generated wide-band NIR signals 222 to the one or more processors 114, electrically communicating 218 the one or more detected wide-band NIR signals 216 to a photo multiplier 112 to accumulate and amplify the one or more detected wide-band NIR signals 216 so that the photo multiplier 112 can electrically communicate 224 one or more amplified detected wide-band NIR signals 226 to the one or more processors 114, and processing 228 the one or more amplified generated wide-band NIR signals 222 and the one or more amplified detected wide-band NIR signals 226 using one or more processors 114 having associated non-transitory tangible computer-readable medium 152 and being operable by the one or more processors 114 to execute a set of instructions 154.

A set of instructions 154 can include, for example, performing DFT 230 on the one or more amplified generated wide-band NIR signals 222 using the one or more processors 114 to define a plurality of input DFT components 232 for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

performing DFT 230 on the one or more amplified detected wide-band NIR signal 226 using one or more processors 114 to define a plurality of detected DFT components 234 for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

and, comparing 236 the plurality of input DFT components 232 with the plurality of detected DFT components 234 in the one or more processors 114 to analyze the associated absorption and scattering of individual wavelengths and associated frequencies in the MPF to define MPF characteristics 206.

Embodiments of a method of the present disclosure also can include, for example, displaying 238 the MPF characteristics 206 on one or more displays 116 to enhance measurement and monitoring in oil-related operations within the portion of the pipe. These displays 116 can be, for example, coupled to PC 156, DSP 158, or ASIC 160, or they can be remote and coupled via electrical wires 124 or wirelessly to another location using, for example, a smartphone 155 or other device.

Where the MPF 400 is scattering, embodiments of a system of the present disclosure to characterize MPF 400 and to enhance measuring and monitoring for oil-related operations can include, for example, a flow director 302; a wide-band NIR source 300 that further can include, for example, a wide-band NIR emitter 304, a splitter 301, one or more optical switches 303, one or more optical windows 308, and one or more optic fibers 307 connecting the same; one or more wide-band NIR detectors 306; a photo multiplier 312; one or more processors 314; and one or more displays 316.

The flow director 302 can be made of metal or silicon, for example, and is anchored within the inside of a portion of a pipe 318 through which MPF 400 flows. The walls 320 of the flow director can be hollow and can also contain optic fibers 322 and electrical wires 324 within it. The flow director 302 can, for example, conduct an electrical signal 412 across its outer surface 328 so that a signal 412 conveyed through an optic fiber 322 or electrical wire 324 from within it can be in direct contact with the MPF 400 as the MPF 400 contacts the outer surface 328 of the flow director 302 within the portion of the pipe 318. The flow director 302 can be shaped like a closed cylindrical tube having two ends 330, 332. The largest circumference 334 of the flow director 302 can be smaller than the circumference 336 of the inner surface 338 of the portion of the pipe 318 carrying MPF 400.

The flow director 302 can have a hollow or solid interior 339, for example, and the interior 339 can also contain various other features of the present disclosure, including for example, wide-band NIR sources 300 or emitters, a splitter 301, optical switches 303, optical fibers 307, and other electronics. Each end 330, 332 of the flow director 302 can be rounded or pointed to facilitate MPF 400 traveling past the first end 330 in the direction of the MPF 400. The emitter 304, plurality of detectors 306, and other electronics can be positioned approximately in the middle 340 of the flow director 302 to enable the MPF 400 to pass by the emitter 304, detectors 306, and other electronics as MPF 400 passes between flow director 302 and the inner surface 338 of the portion of the pipe 318 at the largest point of circumference 334, and at the shortest distance to the inner surface 338 of the portion of the pipe 318, of the flow director 302.

The flow director 302 is anchored within the portion of the pipe 318 using anchors 342 or fasteners. These anchors 342 or fasteners, for example, also can be hollow or manufactured to facilitate optic fibers 322 and electrical wires 324 within them to be in electric communication with the flow director 302. The flow director 302 and the anchors 342 can be manufactured as a single structure, or as separate structures that are later fastened together using commercially acceptable means, including, for example, by welding, soldering, and gluing.

Embodiments of a system of the present disclosure can include, for example, a wide-band NIR source 300 that can further include, for example, a splitter 301, one or more optical switches 303, a controller 313, one or more optical windows 308, and one or more optical fibers 307.

Embodiments of the wide-band NIR source 300 can include a wide-band NIR emitter 304 for generating a wide-band NIR signal 412. This emitter 304 can be positioned, for example, within the portion of the pipe 318 conducting MPF 400, and further within the interior 339 of the flow director 302 and attached using one or more optic fibers 307. This emitter 304 generates a wide-band NIR signal 412 having a wavelength, for example, between approximately 350 and 2500 nanometers, and a narrow beam angle (less than approximately 5 degrees). Wide-band NIR signals 412 having these wavelengths, which are useful for measuring the absorption of relative concentrations of the energy among different kinds of oils and water. As shown in FIG. 11, absorption of NIR waves is higher and different for each respective kind of oil 1102, 1104 at smaller wavelengths, whereas absorption of NIR waves is higher for water 1106 at larger wavelengths.

Embodiments of the wide-band NIR source 300 also can include a splitter 301 positioned, for example, within the portion of the pipe 318 conducting MPF 400, and further within the interior 339 of the flow director 302, and adjacent the wide-band NIR emitter 304 and coupled using one or more optic fibers 307. The splitter 301 eliminates one or more low intensity wide-band NIR signals from the generated wide-band NIR signal 412 and promotes optical transmission of a high intensity wide-band NIR signal 415 to one or more optical switches 303 using the one or more optical fibers 307.

Embodiments of the wide-band NIR source 300 also can include one or more optical switches 303 electronically coupled to a controller 313 and positioned within the portion of the pipe 318 conducting MPF 400, and further within the interior 339 of the flow director 302, and adjacent to the splitter 301 and coupled using one or more optic fibers 307. The one or more optical switches 303 and the controller 313, collectively, enhance the transmission of a single high intensity wide-band NIR signal 415 to one or more optical windows 308 using the one or more optic fibers 307.

Embodiments of the wide-band NIR source 300 also can include one or more optic fibers 307 to connect any of the wide-band NIR emitter 304, the splitter 301, the one or more optical switches 303, and the flow director 302. The optic fibers 307 are in direct contact with the MPF 400 through the walls 320 of the flow director 302, which can be hollow and further can contain the one or more optic fibers 307. The one or more optic fibers 307 convey optical signals, which can include high intensity wide-band NIR signals 415.

Embodiments of a system of the present disclosure can include, for example, one or more optical windows 308 mounted, for example, on the flow director 302 within the portion of the pipe 318 conducting MPF 400. Each optical window 308, for example, can be spaced-apart from another optical window 308 along the flow director 302 all around the circumference 336 of the portion of the pipe 318. The one or more optical windows 308 enhance the transmission of the high intensity wide-band NIR signal 415 through the MPF 400 to the one or more wide-band NIR detectors 306.

Embodiments of a system of the present disclosure also further can include one or more wide-band NIR detectors 306 mounted on the outside surface 348 of, or integral with, a portion of the pipe 318 conveying MPF 400. Each detector 306 can be spaced-apart from another detector 306 and correspondingly paired with the one or more optical windows 308 mounted on the flow director 302. Each detector 306 can have, for example, an optical sensing interface 310, each for enhancing receiving of one or more high intensity wide-band NIR signals 415. The detectors 306 can be in electric communication with electronics for signal processing, including, for example, a photo multiplier 312 and one or more processors 314.

The flow director 302 can be anchored from inside the portion of the pipe 318, and can further be positioned, for example, circumferentially within and closely adjacent to the inside surface 338 of the portion of the pipe 318. When the MPF 400 travels through the portion of the pipe 318 containing the flow director 302, the flow director 302 directs the MPF 400 towards the inner surface 338 of the portion of the pipe 318 so that the MPF 400 passes between the paired optical windows 308 and wide-band NIR detectors 306. This positioning of the flow director 302 within the portion of the pipe 318 enables embodiments of the system and the method of the present disclosure to accurately measure MPF 400 through a portion of a pipe 318 at a full range of water cut (from 0-100%) for oil 401, water 402, and gas 404. Even in a portion of a pipe 318 having a large diameter 350, the closely adjacent positioning of the flow director 302 to the inner surface 338 of the portion of the pipe 318, and therefore the close positioning of each pair of optical windows 308 and wide-band NIR detectors 306, will facilitate the high intensity wide-band NIR signal 415 to penetrate the MPF 400 by minimizing the distance between the paired optical windows 308 and wide-band NIR detectors 306. The flow director 302 will force all the MPF 400 from the annulus which will result in increasing the speed of the MPF. The ratio (f/v) of the frequency (f) of the NIR signal to the fluid velocity of the MPF (v) will still be very high to effectuate desired measurements. These measurements can include, for example, the amount of energy that is absorbed, reflected, and scattered by the MPF 400. Those MPF characteristics 406 (for example, the amount of energy that is absorbed, reflected, and scattered), then can be electrically communicated from the detectors 306 to a photo multiplier 312 and one or more processors 314 for analysis and output.

Embodiments of a system of the present disclosure also further can include, for example, a photo multiplier 312 in electronic communication with the one or more wide-band NIR detectors 306. A photo multiplier 312 or similar amplification element can be used to accumulate and amplify the one or more high intensity wide-band NIR signals 415 received by the detectors 306. Once the signal 415 has been amplified, it can be electronically communicated to one or more processors 314.

Embodiments of a system of the present disclosure also can include one or more processors 314 having non-transitory tangible computer-readable medium 352 associated and being operable by the one or more processors 314 to execute a set of instructions 354. These one or more processors 314 can be found, for example, in a smartphone 355, PC 356, DSP 358, or ASIC 360. The set of instructions 354 (software) can include, for example, processing responsive to the detected one or more wide-band NIR signals 416, to determine a plurality of wavelengths and corresponding frequencies associated with the detected one or more wide-band NIR signals 416; and analyzing the plurality of wavelengths and frequencies to determine corresponding absorption and scattering associated with the detected one or more wide-band NIR signals 416 so that the absorption and scattering define a plurality of MPF characteristics 406 associated with the MPF 400 through the portion of the pipe 318.

The processing further comprises converting the time domain signal into the frequency domain by performing the operation of DFT using the one or more processors 314. Given a sequence of N samples f(n), indexed by n=0 . . . N−1, the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

The one or more processors 314 will compare the DFT of the input signal 432 with the detected DFT components 434 to analyze the associated absorption and scattering of individual wavelength and frequency components in the MPF 400 to define MPF characteristics 406.

Where the MPF 400 is scattering, embodiments of a method of the present disclosure to characterize MPF 400 and to enhance measuring and monitoring for oil-related operations can include, for example, directing the MPF 400 through a portion of a pipe 318 having a flow director 302 positioned circumferentially within the portion of the pipe 318 and closely adjacent to an inner surface 338 of the portion of the pipe 318 so that a full range of water cut flows between the flow director 302 and the inner surface 338 of the portion of the pipe 318.

Embodiments of a system of the present disclosure also can include, for example, controlling 409 a wide-band NIR source 300 to account for scattering properties of the MPF 400 also including, for example, inputting 410 a wide-band NIR signal 412 generated from a wide-band NIR emitter 304 positioned within the portion of the pipe 318, and further within the interior 339 of the flow director 302, to generate a wide-band NIR signal 412, the generated wide-band NIR signal 412 optically conveyed 411 to a splitter 301 using a plurality of optic fibers 307; splitting 413 the generated wide-band NIR signal 412 using a splitter 301 positioned within the portion of the pipe 318, and further within the interior 339 of the flow director 302, to eliminate a plurality of low intensity NIR signals from the generated wide-band NIR signal 412 and promote optical transmission 411 of a high intensity wide-band NIR signal 415 to a plurality of optical switches 303, positioned within the portion of the pipe 318, and further within the interior 339 of the flow director 302, using the plurality of optic fibers 307; and coordinating 409 selective transmission of a high intensity wide-band NIR signal 415 using a plurality of optical switches 303 and a controller 313 to convey 411 the high intensity wide-band NIR signal 415 to a plurality of optical windows 308.

In some embodiments, the single high intensity source is about equal to a number N multiplied by the low intensity source, where N is the number of low intensity signals that the higher intensity signal will be replacing. The low intensity source(s) can be replaced using relative intensity.

Embodiments of a method of the present disclosure also can include, for example, enhancing 419 transmission and reception of the high intensity wide-band NIR signal 415 using the plurality of optical windows 308 mounted on and spaced-apart along the flow director 302 within the portion of the pipe 318 so that the high intensity wide-band NIR signal 415 penetrates the MPF 400 as MPF 400 travels through the portion of the pipe 318, and detecting 414 the high intensity wide-band NIR signal 415 using a plurality of wide-band NIR detectors 306 mounted on and spaced-apart along the outside surface of the portion of the pipe 318 and being correspondingly paired with the plurality of optical windows 308 positioned within the portion of the pipe 318 so that the detected high intensity wide-band NIR signal 416 can be processed.

Embodiments of a method of the present disclosure also can include, for example, electrically communicating 418 the high intensity wide-band NIR signal 415 to a photo multiplier 312 to accumulate and amplify 420 the high intensity wide-band NIR signal 415 to define an amplified high intensity wide-band NIR signal 422 so that the photo multiplier can electrically communicate 424 an amplified high intensity wide-band NIR signal 422 to the one or more processors 314, electrically communicating 418 the detected high intensity wide-band NIR signal 416 to a photo multiplier 312 to accumulate and amplify 420 the detected high intensity wide-band NIR signal 416 so that the photo multiplier 312 can electrically communicate 424 an amplified detected wide-band NIR signal 426 to the one or more processors 314, and processing 428 the amplified high intensity wide-band NIR signal 422 and the amplified detected wide-band NIR signal 426 using one or more processors 314 having associated non-transitory tangible computer-readable medium 352 and being operable by the one or more processors 314 to execute a set of instructions 354.

The set of instructions 354 can include, for example, performing DFT 430 on the amplified high intensity wide-band NIR signal 422 using the one or more processors 314 to define a plurality of input DFT components 432 for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

performing DFT 430 on the amplified detected high intensity wide-band NIR signal 426 using the one or more processors to define a plurality of detected DFT components 434 for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N} \qquad \text{Eq. (6)}$$

and, comparing 436 the plurality of input DFT components 432 with the plurality of detected DFT components 434 to analyze the associated absorption and scattering of individual wavelengths and associated frequencies in the MPF 400 to define MPF characteristics 406.

Embodiments of a method of the present disclosure also can include, for example, displaying 438 the MPF characteristics 406 on one or more displays 316 to enhance measurement and monitoring in oil-related operations within the portion of the pipe 318.

The singular forms "a," "an," and "the" include plural referents, unless the context clearly dictates otherwise.

The foregoing disclosure and description of the disclosure is illustrative and explanatory of the embodiments of the disclosure. Various changes in the details of the illustrated embodiments can be made within the scope of the appended claims without departing from the true spirit of the disclosure. The embodiments of the present disclosure should only be limited by the following claims and their legal equivalents.

The invention claimed is:

1. A system to characterize multiphase flow (MPF) of fluid and enhance measuring and monitoring a full range of water cut for the total flow volume in a portion of a pipe for oil-related operations, the system comprising:
   a flow director anchored within a portion of a pipe and positioned circumferentially within and closely adjacent an inner surface of the pipe to direct MPF through the portion of the pipe for a full range of water cut towards the inner surface of the portion of the pipe;
   a plurality of wide-band Near-Infra Red (NIR) sources, coupled to and positioned spaced-apart along the flow director within the portion of the pipe, to generate one or more wide-band NIR signals;
   a plurality of wide-band NIR detectors, mounted to and positioned circumferentially along an outer surface of the portion of the pipe and being correspondingly paired through at least one optical window with the plurality of wide-band NIR sources positioned within the portion of the pipe, to detect the one or more generated wide-band NIR signals passing through a medium;
   a photo multiplier electrically coupled to the plurality of wide-band NIR detectors to accumulate and amplify each of the generated one or more wide-band NIR signals and the detected one or more wide-band NIR signals;
   one or more processors electrically coupled to the photo multiplier and having associated non-transitory tangible computer-readable medium and being operable by the one or more processors to execute a set of instructions comprising:
      processing responsive to each of an amplified generated one or more wide-band NIR signals and an amplified detected one or more wide-band NIR signals, to determine a plurality of wavelengths and corresponding frequencies associated with each of the amplified generated one or more wide-band NIR signals and the amplified detected one or more wide-band NIR signals, and
      analyzing the plurality of wavelengths and frequencies to determine corresponding absorption and scattering associated with each of the amplified generated one or more wide-band NIR signals and the amplified detected one or more wide-band NIR signals so that the absorption and scattering define a plurality of MPF characteristics associated with the MPF through the portion of the pipe; and
   one or more displays in communication with the one or more processors to display MPF characteristics to measure and monitor in oil-related operations within the portion of the pipe.

2. The system of claim 1, where MPF of fluid comprises non-scattering medium, and where each respective wide-band NIR detector of the plurality of wide-band NIR detectors has an optical window and an optical sensing interface positioned to enhance detecting of the generated one or more wide-band NIR signals.

3. The system of claim 1, where the generated one or more wide-band NIR signals has a wavelength in a range of about 350 to 2000 nanometers, has a narrow beam angle of five degrees or less, and penetrates MPF of fluid without significant scattering properties, and where the flow director further is positioned closely adjacent an inner surface of the pipe to enhance close pairing of the plurality of wide-band NIR sources with the plurality of wide-band NIR detectors so that the generated one or more wide-band NIR signals penetrates the MPF.

4. The system of claim 1 further comprising one or more anchors coupled to the pipe to anchor the flow director within the portion of the pipe, provide electrical access in and through the flow director and to the plurality of wide-band NIR sources, and facilitate a plurality of optic fibers being positioned.

5. The system of claim 4, where the flow director comprises a closed cylindrical tube having a circumference just smaller than a circumference of the portion of the pipe in which the flow director is anchored, and having ends shaped to facilitate MPF traveling around the flow director so that MPF is directed between the flow director and the inner surface of the portion of the pipe.

6. The system of claim 1, where the processing responsive to each of the amplified generated one or more wide-band NIR signals and the amplified detected one or more wide-band NIR signals comprises:

performing one or more DFT operations on the amplified generated one or more wide-band NIR signals using the one or more processors to define a plurality of input DFT components for a sequence of N samples f(n), indexed by n=0 . . . N−1, where the DFT operation is defined as F(k), where k=0 . . . N−1:

$$F(k) = \frac{1}{\sqrt{N}} \sum_{n=0}^{N-1} f(n)e^{-j2\pi kn/N}$$

and, performing one or more DFT operations on the amplified detected one or more wide-band NIR signals using the one or more processors to define a plurality of detected DFT components for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}.$$

7. The system of claim 6, where the analyzing the plurality of wavelengths and frequencies to determine corresponding absorption and scattering associated with each of the amplified generated one or more wide-band NIR signals and the amplified detected one or more wide-band NIR signals further comprises comparing the plurality of input DFT components with the plurality of detected DFT components to characterize associated absorption and scattering of individual wavelengths and associated frequencies in the MPF.

8. A system to characterize MPF of fluid and enhance measuring and monitoring a full range of water cut for the total flow volume in a portion of a pipe through which fluid flows for oil-related operations, the system comprising:

a flow director anchored within a portion of a pipe and positioned circumferentially within and closely adjacent an inner surface of the pipe to direct MPF through the portion of the pipe for a full range of water cut towards the inner surface of the portion of the pipe;

a wide-band Near-Infra Red (NIR) source positioned within an interior of the flow director to directly penetrate the MPF and further comprising:

a wide-band NIR emitter to generate a wide-band NIR signal and optically convey the generated wide-band NIR signal to a splitter over a plurality of optic fibers;

the splitter to eliminate a plurality of low intensity NIR signals from the generated wide-band NIR signal and promote optical transmission of a high intensity wide-band NIR signal to a plurality of optical switches over the plurality of optic fibers;

a plurality of optical switches electrically coupled to a controller, collectively, to enhance transmission of the high intensity wide-band NIR signal to a plurality of optical windows over the plurality of optic fibers;

a plurality of optical windows, coupled to and positioned spaced-apart along the flow director within the portion of the pipe, to enhance detection of the high intensity wide-band NIR signal by a plurality of wide-band NIR detectors;

the plurality of wide-band NIR detectors, mounted to and positioned circumferentially along an outer surface of the portion of the pipe and being correspondingly paired with the plurality of optical windows positioned within the portion of the pipe, to detect the high intensity wide-band NIR signal passing through the MPF of fluid;

a photo multiplier electrically coupled to the controller and the plurality of wide-band NIR detectors to accumulate and amplify each of the high intensity wide-band NIR signal and the detected high intensity wide-band NIR signal;

one or more processors electrically coupled to the controller and the photo multiplier and having associated non-transitory tangible computer-readable medium associated and being operable by the one or more processors to execute a set of instructions comprising:

processing responsive to each of an amplified high intensity wide-band NIR signal and an amplified detected high intensity wide-band NIR signal to determine a plurality of wavelengths and corresponding frequencies associated with each of the amplified high intensity wide-band NIR signal and the amplified detected high intensity wide-band NIR signal, and analyzing the plurality of wavelengths and frequencies to determine corresponding absorption and scattering associated with each of the amplified high intensity wide-band NIR signal and the amplified detected high intensity wide-band NIR signal so that the absorption and scattering define a plurality of MPF characteristics associated with the MPF through the portion of the pipe; and one or more displays in communication with the one or more processors to display the MPF characteristics to enhance measuring and monitoring in oil-related operations within the portion of the pipe.

9. The system of claim 8, where MPF of fluid comprises scattering medium, and where each respective wide-band NIR detector of the plurality of wide-band NIR detectors has an optical sensing interface positioned to enhance detecting of the high intensity wide-band NIR signals.

10. The system of claim 8, where the generated wide-band NIR signal has a wavelength in the range of about 350 to 2000 nanometers and has a narrow beam angle of about five degrees or less, and where the flow director further is positioned closely adjacent an inner surface of the portion of the pipe to enhance close pairing of the plurality of optical windows with the plurality of wide-band NIR detectors so that the high intensity wide-band NIR signal penetrates the MPF.

11. The system of claim 8 further comprising one or more anchors coupled to the portion of the pipe to anchor the flow director within the portion of the pipe, provide electrical access in and through the flow director, and facilitate a plurality of optic fibers being positioned.

12. The system of claim 11, where the flow director comprises a closed cylindrical tube having the interior for housing the wide-band NIR source and having a circumference just smaller than a circumference of the portion of the pipe in which the flow director is anchored, and having ends shaped to facilitate MPF traveling around the flow director so that MPF is directed between the flow director and the inner surface of the portion of the pipe.

13. The system of claim 8, where the processing responsive to each of the amplified high intensity wide-band NIR signal and the amplified detected high intensity wide-band NIR signal comprises:
  performing one or more DFT operations on the amplified high intensity wide-band NIR signals using the one or more processors to define a plurality of input DFT components for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N}$$

and, performing one or more DFT operations on the amplified detected high intensity wide-band NIR signal using the one or more processors to define a plurality of detected DFT components for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n) e^{-j2\pi kn/N}.$$

14. The system of claim 13, where the analyzing of the plurality of wavelengths and frequencies to determine corresponding absorption and scattering associated with each of the amplified high intensity wide-band NIR signal and the amplified detected high intensity wide-band NIR signal further comprises comparing the plurality of input DFT components with the plurality of detected DFT components to characterize associated absorption and scattering of individual wavelengths and associated frequencies in the MPF.

15. A method to directly characterize MPF of fluid and enhance measuring and monitoring a full range of water cut for the total flow volume in a portion of a pipe through which the fluid flows for oil-related operations, the method comprising:
  directing MPF through a portion of a pipe having a flow director positioned circumferentially within the portion of the pipe and closely adjacent an inner surface of the portion of the pipe so that a full range of water cut flows between the flow director and the inner surface of the portion of the pipe;
  inputting a plurality of wide-band Near-Infra Red (NIR) signals generated from a plurality of wide-band NIR sources mounted on and spaced-apart along the flow director that is within the portion of the pipe to penetrates the MPF as fluid flows through the portion of the pipe;
  detecting the generated one or more wide-band NIR signals with a plurality of wide-band NIR detectors mounted on and spaced-apart along an outside surface of the portion of the pipe through at least one optical window and being correspondingly paired with the plurality of wide-band NIR sources positioned within the portion of the pipe so that the detected one or more wide-band NIR signals can be processed;
  electrically communicating the generated one or more wide-band NIR signals to a photo multiplier to accumulate and amplify the generated one or more wide-band NIR signals so that the photo multiplier can electrically communicate amplified generated one or more wide-band NIR signals to the one or more processors;
  electrically communicating the detected one or more wide-band NIR signals to a photo multiplier to accumulate and amplify the detected one or more wide-band NIR signals so that the photo multiplier can electrically communicate amplified detected one or more wide-band NIR signals to the one or more processors;
  processing each of the amplified generated one or more wide-band NIR signals and the amplified detected one or more wide-band NIR signals using the one or more processors having associated non-transitory tangible computer-readable medium and being operable by the one or more processors to execute a set of instructions comprising:
    processing responsive to each of the amplified generated one or more wide-band NIR signals and the amplified detected one or more wide-band NIR signals, to determine a plurality of wavelengths and corresponding frequencies associated with each of the amplified generated one or more wide-band NIR signals and the amplified detected one or more wide-band NIR signals, and
    analyzing the plurality of wavelengths and frequencies to determine corresponding absorption and scattering associated with each of the amplified generated one or more wide-band NIR signals and the amplified detected one or more wide-band NIR signals so that the absorption and scattering define a plurality of MPF characteristics associated with the MPF through the portion of the pipe; and
  displaying the MPF characteristics on one or more displays to enhance measurement and monitoring in oil-related operations within the portion of the pipe.

16. The method of claim 15, where the MPF comprises non-scattering medium, and where detecting the generated one or more wide-band NIR signals with a plurality of wide-band NIR detectors is enhanced by an optical sensing interface positioned on each respective wide-band NIR detector of the plurality of wide-band NIR detectors.

17. The method of claim 15, where the generated one or more wide-band NIR signals comprises a wavelength in the range of about 350 to 2000 nanometers and a narrow beam angle of about five degrees or less to penetrate MPF of the non-scattering medium, and where the flow director further is positioned closely adjacent an inner surface of the pipe to enhance close pairing of the plurality of wide-band NIR sources with the plurality of wide-band NIR detectors so that the generated one or more wide-band NIR signals penetrates the MPF.

18. The method of claim 17, where the flow director comprises a closed cylindrical tube for housing the plurality of wide-band NIR sources and having a circumference just smaller than a circumference of the portion of the pipe in which the flow director is anchored, and having ends shaped to facilitate MPF traveling around the flow director so that MPF is directed between the flow director and the inner surface of the portion of the pipe.

19. The method of claim 15, where the processing responsive to each of the amplified generated one or more wide-band NIR signals and the amplified detected one or more wide-band NIR signals comprises:

performing one or more DFT operations on the amplified generated one or more wide-band NIR signals to define a plurality of input DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}$$

and, performing one or more DFT operations on the amplified detected one or more wide-band NIR signal to define a plurality of detected DFT components by the one or more processors for a sequence of N samples f(n), indexed by n=0 . . . N−1, where the DFT is defined as F(k), where k=0 . . . N−1:

$$F(k) = \frac{1}{\sqrt{N}} \sum_{n=0}^{N-1} f(n)e^{-j2\pi kn/N}.$$

20. The method of claim 19, where the analyzing the plurality of wavelengths and frequencies to determine corresponding absorption and scattering associated with each of the one or more amplified generated wide-band NIR signals and the one or more amplified detected wide-band NIR signals comprises comparing the plurality of input DFT components with the plurality of detected DFT components to characterize associated absorption and scattering of individual wavelengths and associated frequencies in the MPF.

21. A method to directly characterize MPF of fluid and enhance measuring and monitoring a full range of water cut for the total flow volume in a portion of a pipe through which fluid flows for oil-related operations, the method comprising:

directing MPF through a portion of a pipe having a flow director positioned circumferentially within the portion of the pipe and closely adjacent an inner surface of the portion of the pipe so that a full range of water cut flows between the flow director and the inner surface of the portion of the pipe;

controlling a wide-band Near-Infra Red (NIR) source positioned within an interior of the flow director to account for scattering properties of the MPF further comprising:

inputting a wide-band NIR signal generated from a wide-band NIR emitter and optically conveying the generated wide-band NIR signal to a splitter over a plurality of optic fibers;

splitting the generated wide-band NIR signal via a splitter to eliminate a plurality of low intensity NIR signals from the generated wide-band NIR signal and promote optical transmission of a high intensity wide-band NIR signal to a plurality of optical switches over the plurality of optic fibers; and coordinating selective transmission of the high intensity wide-band NIR signal via a plurality of optical switches and a controller to convey the high intensity wide-band NIR signal to a plurality of optical windows;

enhancing transmission and reception of the high intensity wide-band NIR signal by the plurality of optical windows mounted on and spaced-apart along the flow director within the portion of the pipe so that the high intensity wide-band NIR signal penetrates the MPF as MPF flows through the portion of the pipe;

detecting the high intensity wide-band NIR signal by a plurality of wide-band NIR detectors mounted on and spaced-apart along the outside surface of the portion of the pipe and being correspondingly paired with the plurality of optical windows positioned within the portion of the pipe so that a detected high intensity wide-band NIR signal can be processed; and electrically communicating the high intensity wide-band NIR signal to a photo multiplier to accumulate and amplify the high intensity wide-band NIR signal so that the photo multiplier can electrically communicate the amplified high intensity wide-band NIR signal to the one or more processors;

electrically communicating the detected high intensity wide-band NIR signal to a photo multiplier to accumulate and amplify the detected high intensity wide-band NIR signal so that the photo multiplier can electrically communicate an amplified detected wide-band NIR signal to the one or more processors;

processing each of the amplified high intensity wide-band NIR signal and the amplified detected wide-band NIR signal by the one or more processors having associated non-transitory tangible computer-readable medium and being operable by the one or more processors to execute a set of instructions further comprising:

processing responsive to each of the amplified high intensity wide-band NIR signal and the amplified detected wide-band NIR signal, to determine a plurality of wavelengths and corresponding frequencies associated with each of amplified high intensity wide-band NIR signal and the amplified detected wide-band NIR signal, and analyzing the plurality of wavelengths and frequencies to determine corresponding absorption and scattering associated with each of the amplified high intensity wide-band NIR signal and the amplified detected wide-band NIR signal so that the absorption and scattering define a plurality of MPF characteristics associated with the MPF through the portion of the pipe; and displaying the MPF characteristics on one or more displays to enhance measurement and monitoring in oil-related operations within the portion of the pipe.

22. The method of claim 21, where inputting a plurality of wide-band NIR signals generated from a plurality of wide-band NIR sources comprises the generated wide-band NIR signal having a wavelength in the range of about 350 to 2000 nanometers and a narrow beam angle of about five degrees or less, and where the flow director further is positioned closely adjacent an inner surface of the portion of the pipe to enhance close pairing of the plurality of optical windows with the plurality of wide-band NIR detectors so that the high intensity wide-band NIR signal penetrates the MPF.

23. The method of claim 22, where the flow director comprises a closed cylindrical tube having the interior for housing the wide-band NIR source and having a circumference just smaller than a circumference of the portion of the pipe in which the flow director is anchored, and having ends shaped to facilitate MPF traveling around the flow director so that MPF is directed between the flow director and the inner surface of the portion of the pipe.

24. The method of claim 21, where the processing responsive to each of the one or more amplified high intensity wide-band NIR signals and the one or more amplified high intensity wide-band NIR signals comprises:
performing one or more DFT operations on the amplified high intensity wide-band NIR signal to define a plurality of input DFT components by the one or more processors for a sequence of N samples f(n), indexed by n=0 ... N−1, where the DFT is defined as F(k), where k=0 ... N−1:

$$F(k) = \frac{1}{\sqrt{N}} \sum_{n=0}^{N-1} f(n) e^{-j2\pi kn/N}$$

and, performing one or more DFT operations on the amplified detected high intensity wide-band NIR signal to define a plurality of detected DFT components by the one or more processors for a sequence of N samples f(n), indexed by n=0 ... N−1, where the DFT is defined as F(k), where k=0 ... N−1:

$$F(k) = \frac{1}{\sqrt{N}} \sum_{n=0}^{N-1} f(n) e^{-j2\pi kn/N}.$$

25. The method of claim 24, where the analyzing the plurality of wavelengths and frequencies to determine corresponding absorption and scattering associated with each of the amplified high intensity wide-band NIR signal and the amplified detected wide-band NIR signal comprises comparing the plurality of input DFT components with the plurality of detected DFT components to characterize associated absorption and scattering of individual wavelengths and associated frequencies in the MPF.

26. A method to directly characterize MPF of fluid and enhance measuring and monitoring a full range of water cut in a portion of a pipe through which the fluid flows for oil-related operations, the method comprising:
directing MPF of fluid through a portion of a pipe closely adjacent an inner surface of the portion of the pipe so that a full range of water cut flows closely adjacent the inner surface of the portion of the pipe, the MPF of fluid further comprising a plurality of components of oil, water, gas, and solid;
controlling a wide-band NIR source positioned within the portion of the pipe to emit a high intensity wide-band NIR signal that penetrates MPF of the fluid as it flows closely adjacent the inner surface of the portion of the pipe;
detecting one or more high intensity wide-band NIR signals by use of a plurality of wide-band NIR detectors mounted on and spaced-apart along the outside surface of the portion of the pipe and correspondingly paired with a plurality of optical windows positioned within the portion of the pipe, the plurality of wide-band NIR detectors and the plurality of optical windows collectively operate to enhance detection of the high intensity wide-band NIR signal as MPF of fluid passes therebetween; and
processing the one or more detected high intensity wide-band NIR signals to determine relative absorption and scatter for each component of the plurality of components in the MPF of fluid relative to a baseline to define one or more MPF characteristics to be displayed on one or more displays and enhance measurement and monitoring in oil-related operations within the portion of the pipe.

* * * * *